US006197503B1

(12) United States Patent
Vo-Dinh et al.

(10) Patent No.: US 6,197,503 B1
(45) Date of Patent: *Mar. 6, 2001

(54) INTEGRATED CIRCUIT BIOCHIP MICROSYSTEM CONTAINING LENS

(75) Inventors: Tuan Vo-Dinh; Alan Wintenberg; Milton N. Ericson, all of Knoxville, TN (US)

(73) Assignee: UT-Battelle, LLC, Oak Ridge, TN (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/979,672

(22) Filed: Nov. 26, 1997

(51) Int. Cl.$^7$ .............................. C12Q 1/68; C12P 19/34; C12N 9/00; C07H 21/04
(52) U.S. Cl. ........................... 435/6; 435/91.1; 435/91.2; 435/183; 435/287.2; 536/23.1; 536/24.3; 536/24.31; 536/24.33
(58) Field of Search .............................. 435/6, 91.1, 91.2, 435/183, 287.2; 436/94; 536/23.1, 24.3, 24.31, 24.33, 25.3

(56) References Cited

U.S. PATENT DOCUMENTS

| 5,156,728 | 10/1992 | Yamaguchi et al. |
| 5,578,832 | 11/1996 | Trulson et al. ................. 250/458.1 |
| 5,605,662 | 2/1997 | Heller et al. ....................... 422/68.1 |
| 5,631,734 | 5/1997 | Stern et al. ........................... 356/317 |
| 5,637,874 | 6/1997 | Honzawa et al. .................... 250/361 |
| 5,783,389 * | 7/1998 | Vo Dinh et al. ........................ 435/6 |

FOREIGN PATENT DOCUMENTS

| WO 93/22678 | 11/1993 | (WO) . |
| WO 97/12030 | 4/1997 | (WO) . |
| WO 97/12225 | 4/1997 | (WO) . |
| WO 99/27140 | 6/1999 | (WO) . |

OTHER PUBLICATIONS

Affymetrix http://www.affymetrix.com; Jul. 23, 1997.
Alarie et al., "Intensified charge couple device–based fiber–optic monitor for rapid remote surface–enhanced Raman scattering sensing," *Appl. Spectrose.*, 46:1608–1612, 1992.
Aubert et al., "Monolithic Optical Position Encoder with On–Chip Photodiodes," *IEEE Journal of Solid State Circuits*, 23(2):465–73, 1988.
Eggars et al., "A microchip for quantitative detection of molecules utilizing luminescent and radioisotope reporter groups," *Biotechniques*, 17:516–523, 1994.
Graham et al., "Gene probe assay on a fibre–optic evanescent wave biosensor," *Biosensors and Bioelectronics*, 7:487–493, 1992.
Hacia et al., "Detection of heterozygous mutations in BRCA1 using high density oligonucleotide arrays and two––colour fluorescence analysis," *Nature Genetics*, Dec. 1996.
Isola et al., "Developement of a Ganasensor for Mycobacterium Tuberculosis," In: Biomedical Sensing Imaging and Tracking Technologies I, Lieberman et al., Eds., *SPIE*, 2676:228–239, 1996.
Kumar et al., "Monitoring oligonucleotide hybridization using light–addressable potentiometric and evanescent wave fluorescence sensing," *Materials Science and Engineering*, C1:187–192, 1994.
Pease et al., "Light–generated oligonucleotide arrays for rapid DNA sequence analysis," *Proc. Natl. Acad. Sci USA*, 91:5022–5026, May 1994.
Piunno et al., "Fiber–optic DNA sensor for fluorometric nucleic acid determination," *Anal. Chem.*, 67(15):2635–2643, 1995.
Piunno et al., "Fiber optic biosensor for fluorimetric detection of DNA hybridization," *Anal. Chim. Acta*, 288:205–214, 1994.
Schena et al., "Quantitative monitoring of gene expression patterns with a complementary DNA microarray," *Science*, 270:467–470, 1995.
Stevenson et al., "Synchronous luminescence: A new detection technique for multiple probes used for DNA sequencing," *Biotechniques*, 16:1104–1110, 1994.
Stipp, "Gene chip breakthrough," *Fortune*, 56–73, Mar. 1997.
Uddin et al., "Fiber optic biosensor for fluorimetric detection of triple–helical DNA," *Nucleic Acids Research*, 25(20):4139–4146, 1997.
Vo–Dinh et al., "Antibody–based fiberoptics biosensor for the carcinogen benzo(a)pyrene," *Appl. Spectrosc.*, 5:735–738, 1987.
Vo–Dinh et al., "Fiber optic fluoroimmunosensors," In: Fiber Optic Chemical Sensors and Biosensors, Wolfbeis, Ed., CRC Press, Boca Raton, Florida, 1991.
Vo–Dinh et al., "Surface–enhanced Raman gene probes," *Anal. Chem.*, 66:3379–3383, 1994.

(List continued on next page.)

Primary Examiner—Kenneth R. Horlick
Assistant Examiner—Jeffrey Siew
(74) Attorney, Agent, or Firm—Williams, Morgan & Amerson, P.C.

(57) ABSTRACT

The present invention discloses a self-contained miniature DNA biosensor designed to detect specific molecular targets, particularly suitable for detection of nucleic acids. For example, hybridized DNA may be detected without external monitoring or signal transmission. The miniaturized biosensor is a biochip comprising multiple biological sensing elements such as DNA probes, excitation microlasers, a sampling waveguide equipped with optical detectors (fluorescence and Raman), integrated electrooptics, and a biotelemetric radio frequency signal generator. The novel integrated circuit biochip microsystem (ICBM) is suitable for gene analysis and will allow rapid, large-scale, and cost-effective production of gene biochips.

17 Claims, 17 Drawing Sheets

OTHER PUBLICATIONS

Ackens et al., "A compact and flexible CCD readout-system," IEEE Nuclear Science Symposium Conference Record, 1998.

Downs, "Prospects for nucleic-acid biosensors," *Biochem. Soc. Trans.*, 19:39–43, 1991.

Fodor et al., "Light-directed, spatially addressable parallel chemical synthesis," *Science*, 251:767–773, 1991.

International Search Report dated Apr. 13, 1999 (PCT/US98/25294; 4310.002410).

Isola et al., "Surface-enhanced Raman gene probe for HIV detection," *Anal. Chem.*, 70:1352–1356, 1998.

Kung et al., "Picogram quantitation of total DNA using DNA-binding proteins in a silicon sensor-based system," *Anal. Biochem.*, 187:220–227, 1990.

Nanogen Website on the World Wide Web at http://www.nanogen.com.

Simpson et al., "Bioluminescent bioreporter integrated circuits (BBICs): Whole-cell chemical biosensors," Solid State Sensor and Actuator Workshop, Jun. 8–11, 1998.

Simpson et al., "Bioluminescent-bioreporter integrated circuits from novel whole-cell biosensors," *TIBTECH*, 16:332–338, 1998.

Vo-Dinh et al., "Development of a DNA biochip for gene diagnosis," Proceedings of Biomedical Sensing and Imaging Technologies, San Jose, California, Jan. 26–27, 1998.

Eggers and Ehrlich, "A review of microfabricated devices for gene-based diagnostics," *Hematol. Pathol.*, 9(1):1–15, 1995.

Eggers et al., "A microchip for quantitative detection of molecules utilizing luminescent and radioisotope reporter groups," *Biotechniques*, 17(3):516–525, 1994.

Ehrlich and Matsudaira, "Microfluidic devices for DNA analysis," *Trends Biotechnol.*, 17(8):315–319, 1999.

Schmalzing et al., "Recent developments in DNA sequencing by capillary and microdevice electrophoreis," *Electrophoresis*, 20(15–16):3066–3077, 1999.

Schmalzing et al., "DNA sequencing on microfabricated electrophoretic devices," *Anal. Chem.*, 70(11):2303–2310, 1998.

Schmalzing et al., "DNA typing in thirty seconds with a microfabricated device," *Proc. Natl. Acad. Sci. USA*, 94(19):10273–10278, 1997.

Written Opinion mailed Sep. 22, 1999 (PCT/US98/25294; 4310.002410).

* cited by examiner

SEQUENCE LISTING (1) GENERAL INFORMATION:

(iii) NUMBER OF SEQUENCES: 2

(2) INFORMATION FOR SEQ ID NO:1:

(i) SEQUENCE CHARACTERISTICS:
      (A) LENGTH: 20 base pairs
      (B) TYPE: nucleic acid
      (C) STRANDEDNESS: single
      (D) TOPOLOGY: linear (ix) FEATURE:
      (A) NAME/KEY: modified_base
      (B) LOCATION: 10
      (D) OTHER INFORMATION: /note= "r = A or G"

(xi) SEQUENCE DESCRIPTION: SEQ ID NO:1:

CCTCCTCCTR CCCAGCAGGG    20

```
(2) INFORMATION FOR SEQ ID NO:2:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:2:

CCTCCTCCTT CCCAGCAGGG                                            20
```

INTEGRATED CIRCUIT BIOCHIP MICROSYSTEM CONTAINING LENS

BACKGROUND OF THE INVENTION

1. Field of the Invention

This invention relates to novel biochips that combine integrated circuit elements, electro-optical excitation and detection systems, and molecular receptor probes in a self-contained integrated microdevice.

2. Description of Related Art

Much interest has centered on the development of DNA chips based on high density oligonucleotide arrays and fluorescence analysis such as described by Hacia et al. (J. G. Hacia, L. C. Brody, M. S. Chee. S. P. A. Fodor F. S. Collins in *Nature Genetics* Dec. 14, 1996). This principle has been commercialized in the Affymetrix® GeneChip® which was developed to process large amounts of genetic information. GeneChip® probe arrays are arranged on single chips in the form of tens of thousands of DNA probes that are designed to fluorescence when hybridized to their targets. The light is scanned with laser light and the light intensity stored for later computations (Jul. 23, 1997, Affymetrix http://www.affymetrix.com/).

Unfortunately, the DNA chips, while much like the microprocessor chips that currently run today's technology, have yet to be successfully developed into integrated systems that conveniently interpret what information can be captured by DNA chips. Thus, an Affymetrix® chip that is stated to detect HIV mutations still requires an external scanning and interpretation of the signals that are generated by a DNA-captured nucleic acid.

The detection of biological species in complex systems is important for many biomedical and environmental applications. In particular, there is a strong interest in developing detection techniques and sensors for use in such applications as infectious disease identification, medical diagnostics and therapy, as well as biotechnology and environmental bioremediation. An objective in developing new techniques and sensors is not only to be able to selectively identify target compounds but to be able to assay large numbers of samples. Yet, there remain problems in reproducibly detecting and measuring low levels of biological compounds conveniently, safely and quickly.

A basic interest has been in the development of inexpensive biosensors for environmental and biomedical diagnostics. Biosensors have been investigated, mostly based on DNA probes and on various systems for analysis of oligonucleotide arrays, but there appears to be limited consideration and development of integrated circuit (IC) gene probe-based biosensors on microchips. Existing systems typically employ photomultipliers or 2-dimensional detectors such as charge-coupled device (CCD) systems which require bulky electronic and data conditioning accessories (Affymetrix® http, 1997; Schena, et al., 1995; Piunno, et al., 1995; Kumar, et al, 1994; Eggars, et al., 1994; and, Graham, et al., 1992).

There are several methods for selectively identifying biological species, including antibody detection and assay as in the well-known Enzyme-linked Immunosuppresent Assays (ELISA) employing molecular hybridization techniques. Generally speaking, it is possible to identify sequence-specific nucleic acid segments, and to design sequences complementary to those segments, thereby creating a specific probe for a target cell, such as different pathogen cells or even mammalian cells that have mutated from their normal counterparts. In principle, one can design complementary sequences to any identified nucleic acid segment. In many instances, unique sequences specific to an organism may be used as probes for a particular organism or cell type. The quantitative phenotypic analysis of yeast deletion mutants, for example, has utilized unique nucleic acid sequence identifiers to analyze deletion strains by hybridization with tagged probes using a high-density parallel array (Shoemaker et al., 1996).

Hybridization involves joining a single strand of nucleic acid with a complementary probe sequence. Hybridization of a nucleic acid probe to nucleic acid sequences such as gene sequences from bacteria, or viral DNA offers a very high degree of accuracy for identifying nucleic acid sequences complementary to that of the probe. Nucleic acid strands tend to be paired to their complements in double-stranded structures. Thus, a single-stranded DNA molecule will seek out its complement in a complex mixture of DNA containing large numbers of other nucleic acid molecules. Hence, nucleic acid probe (e.g., gene probe) detection methods are very specific to DNA sequences. Factors affecting the hybridization or reassociation of two complementary DNA strands include temperature, contact time, salt concentration, the degree of mismatch between the base pairs, and the length and concentration of the target and probe sequences. In perhaps the simplest procedure, hybridization is performed on an immobilized target or a probe molecule attached on a solid surface such as a nitrocellulose or nylon membrane or a glass plate.

Despite significant strides in developing DNA chips, detection and analysis methods have not been well developed to take advantage of the amount of information that such chips can obtain in a short period of time. A common technique for detecting DNA probes involves labeling the probe with radioactive tags and detecting the probe target hybrids by autoradiography. Phosphorous-32 ($^{32}$P) is the most common radioactive label used because of its high-energy emission and, consequently short exposure time. Radioactive label techniques, however, suffer several disadvantages, such as limited shelf life. For example, $^{32}$P has a limited shelf life because it has a 14-day half-life.

Several optical detection systems based on surface-enhanced Raman fluorescence of visible and near-infrared (NIR) dye probe labels have been investigated (Vo-Dinh, et al., 1987 and Isola, et al., 1996) for non-radioactive detection of tagged gene probes. Fluorescence detection is extremely sensitive when the target compounds or labeled systems are appropriately selected. Indeed, a zeptomole ($10^{-21}$ mole) detection limit has been achieved using fluorescence detection of dyes with laser excitation (Stevenson, et al., 1994). Even so, detection systems are macro compared to the micro world of DNA arrays, as many detection/analysis methods are mere adaptations from other systems. This means that analysis is relatively slow, compared to data accumulation.

There is therefore a distinct need for development of systems that will allow rapid, large-scale and cost effective use of recently developed DNA biochips.

SUMMARY OF THE INVENTION

The invention in its broadest aspect comprises an integrated microchip biosensor device. Such a device employs multiple optical sensing elements and microelectronics on a single integrated chip combined with one or more nucleic acid-based bioreceptors designed to detect sequence specific genetic constituents in complex samples. The microchips combine integrated circuit elements, electrooptics, excitation/detection systems and nucleic acid-based receptor probes in a self-contained and integrated microdevice. A basic biochip, for example, may include: (1) an excitation light source; (2) a bioreceptor probe; (3) a sampling element; (4) a detector; and (5) a signal amplification/treatment system.

The integrated circuit biomicrochips of the present invention comprise an integrated circuit that includes an optical transducer and associated optics and circuitry for generating an electrical signal in response to light or other radiation indicative of the presence of a target biological species, particularly a nucleic acid. The chip may also include a support for immobilizing a bioprobe, which is preferably a nucleic acid. In particular embodiments, a target nucleic acid may be tagged or labeled with a substance that emits a detectable signal; for example, luminescence. Alternatively, the bioprobe attached to the immobilized bioprobe may be tagged or labeled with a substance that emits a detectable or altered signal when combined with the target nucleic acid. The tagged or labeled species may be fluorescent, phosphorescent, or otherwise luminescent, or it may emit Raman energy or it may absorb energy.

The highly integrated biosensors of the present invention are advantageous in part because of fabricating multiple optical sensing elements and microelectronics on a single integrated circuit, and further combining the chip in preferred embodiments with a plurality of molecular hybridization probes (Geiger, et al., 1990 and Aubert, et al., 1988). When the probes selectively bind to a targeted species, a signal is generated that is picked up by the chip. The signal may then be processed in several ways, depending on the nature of the signal.

In one aspect, the present invention concerns an integrated system that includes (1) a targeted nucleic acid sequence in combination with a biological probe which is modified to receive light or other radiation of a first frequency and thereby to emit light or other radiation of a different frequency than the first frequency, and (2) to detect the emitted radiation by means of a phototransducer. The target nucleic acid is typically a uniquely characteristic gene sequence of a pathogen such as a fungus, bacteria, or virus, or other distinct nucleic acid species such as may be found in mutant mammalian cells or in individuals with inherited errors of metabolism. The target nucleic acid is modified or labeled to include a tag or label that emits a signal upon exposure to an incident light or other radiation.

The target nucleic acid may be immobilized onto the integrated microchip that also supports a phototransducer and related detection circuitry. Alternatively, a gene probe may be immobilized onto a membrane or filter which is then attached to the microchip or to the detector surface itself, such as the transducer detector described herein. This approach avoids the need to bind the bioreceptor directly to the transducer and thus is attractive for simplifying large-scale production In one preferred embodiment of the invention, light of a highly directional or focused nature is impinged on a target nucleic that inherently or by virtue of an appropriate tag or label will emit a detectable signal upon irradiation. The irradiation may be provided by a suitable light source, such as a laser beam or a light-emitting diode (LED). With the Raman, fluorescence and phosphorescence detection modes, the incident light is further kept separate from the emitted light using different light paths and/or appropriate optical filters to block the incident light from the detector.

A target nucleic acid sequence is preferably hybridized with a nucleic acid sequence that is selected for that purpose (bioprobe). As stated earlier, the selected bioprobe is immobilized on a suitable substrate, either on the biochip itself or on a membrane type material that is then contacted or attached to the chip surface. The bioprobe may be labeled with a tag that is capable of emitting light or other non-radioactive energy. Upon hybridization with a target nucleic acid sequence, the hybrid product can be irradiated with light of suitable wavelength and will emit a signal in proportion to the amount of target nucleic acid hybridized, see FIG. 20. The labeled bioprobe may comprise a labeled molecular bioreceptor. Known receptors are advantageous to use because of their known ability to selectively bind with the target nucleic acid sequence. In certain particular examples, the bioreceptor itself may exhibit changes in light emission when its cognate is bound.

In certain applications, it may be desirable to increase the amount of biotarget when only trace quantities are present in a sample. The present invention is compatible with polymerase chain reaction (PCR), which is a technique to amplify DNA sequences.

BRIEF DESCRIPTION OF THE DRAWINGS

For a more complete understanding of the present invention and the advantages thereof, reference is now made to the following description taken in conjunction with the accompanying drawings in which like reference numbers indicate like features and wherein.

DESCRIPTION OF ILLUSTRATIVE EMBODIMENTS

Definitions

Figure 1:
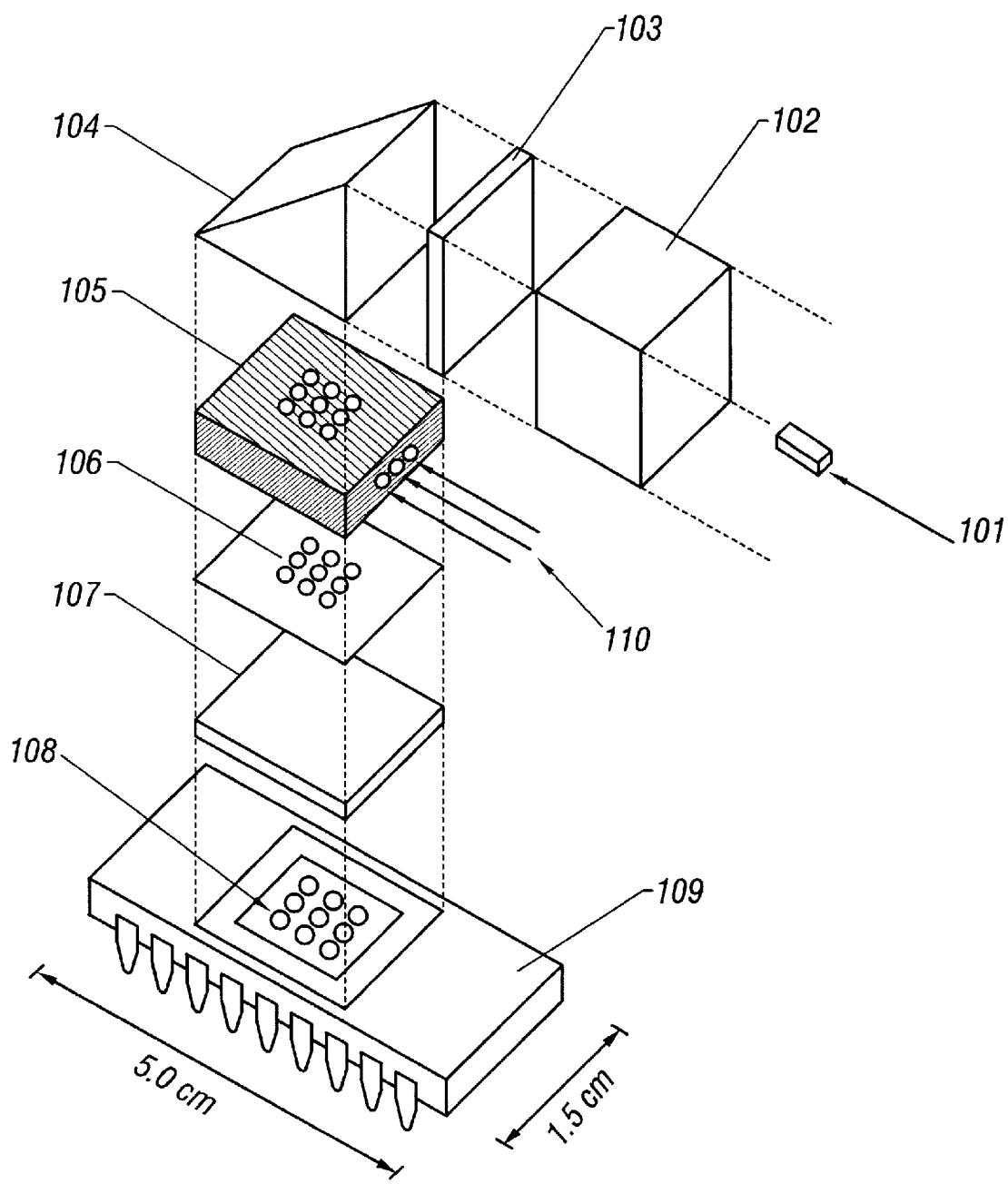
FIG. 1 illustrates a schematic, exploded view of an example of a DNA biochip of the invention.

An integrated circuit (IC) is a circuit comprised of elements such as transistors, resistors and capacitors fabricated in a single piece of semiconducting material, usually silicon or gallium arsenide. As used herein, "integrated circuit" not only refers to the common definition but also to highly integrated structures including, for example:

1) multichip modules where several IC's and other circuit elements including molecular target probes may be combined compactly on a polymer, quartz, glass, sliver, ceramic or other substrates. In some cases, one IC may be the substrate with other components, such as photodiodes or LEDs mounted on it;

2) Hybrid microcircuits where one or more IC's and other circuit elements are mounted on or several substrate(s); and, 3) Other compact electromechanical arrangements of a circuit comprising primarily one but possibly more IC's and other electronic components and microelectromechanised systems (MEMs).

Biosensor Probes

The development of biosensor technologies for detection of trace quantities of biological species in complex systems is important for many biomedical and environmental applications. Spectroscopic chemical sensors and biosensors have been developed using laser induced fluorescence, room temperature phosphorescence, surface enhanced Raman spectroscopy, antibody based immunofluorescence and gene probe Raman sensing methods, including gene probes having surface-enhanced Raman scattering labels to enhance the selectivity and sensitivity of chemical sensors and biosensors (Vo-Dinh et al., 1994).

The present invention uses spectroscopic techniques such as luminescence with visible and NIR labels is a useful detection scheme for gene biosensors without having the limitation of radioactive methods.

Non-radioactive probes, particularly gene probes, are desirable because of their selectivity in addition to avoiding the hazards involved with radioactive materials. Recognition and detection of biological species is based on the principle that cell specific nucleic acid sequences can be specifically recognized and can be combined with a receptor that specifically binds with that species. Such receptors include, for example, antibodies, enzymes, cells, bacterial probes, complementary nucleic acids, or nucleic acids that selectively hybridize with a cell-specific nucleic acid sequence. Receptors may be found and employed in the form of organelles, tissue components, chemoreceptors or even whole cells or microorganisms. Other types of receptors may include biomimetic materials such as cyclodextrins, molecular imprint materials, etc.

Gene probes operate on a hybridization process. Hybridization involves joining of a single strand of nucleic acid with a complementary probe sequence. Hybridization of a nucleic acid probe to a biotarget such as bacterial or viral DNA or RNA or selected gene segments, offers a high degree of accuracy for identifying nucleic acid sequences complementary to the probe. Nucleic acid strands tend to be paired with complementary strands, such as is typically found in double-stranded DNA structures. Therefore, a single-stranded DNA (or RNA) will seek out its complement in a complex mixture of DNA containing large numbers of other nucleic acid molecules. Nucleic acid probe or gene probe detection methods are specific to DNA sequences.

Factors affecting the hybridization or reassociation of two complementary DNA strands include temperature, contact time, salt concentration, the degree of mismatch between the base pairs, and the length and concentration of the target and probe sequences.

Immobilization Techniques

Biologically active DNA probes may be directly or indirectly immobilized onto a transducer detection surface to ensure optimal contact and maximum detection. When immobilized onto a substrate, the gene probes are stabilized and therefore may be used repetitively. In general terms, hybridization is performed on an immobilized nucleic acid target or a probe molecule is attached to a solid surface such as nitrocellulose, nylon membrane or glass. Numerous other matrix materials may be used, including reinforced nitrocellulose membrane, activated quartz, activated glass, polyvinylidene difluoride (PVDF) membrane, polystyrene substrates, polyacrylamide-based substrate, other polymers such as poly(vinyl chloride), poly(methyl methacrylate), poly(dimethyl siloxane), photopolymers (which contain photoreactive species such as nitrenes, carbenes and ketyl radicals capable of forming covalent links with target molecules (Saiki, et al., 1994).

Binding of the bioprobe to a selected support may be accomplished by any of several means. For example, DNA is commonly bound to glass by first silanizing the glass surface, then activating with carbodimide or glutaraldehyde. Alternative procedures may use reagents such as 3-glycidoxypropyltrimethoxysilane (GOP) or aminopropyltrimethoxysilane (APTS) with DNA linked via amino linkers incorporated either at the 3' or 5' end of the molecule during DNA synthesis. DNA may be bound directly to membranes using ultraviolet radiation. With nitrocellous membranes, the DNA probes are spotted onto the membranes. A UV light source (Stratalinker, from Stratagene, La Jolla, Calif.) is used to irradiate DNA spots and induce cross-linking. An alternative method for cross-linking involves baking the spotted membranes at 80° C. for two hours in vacuum.

Gene bioprobes may first be immobilized onto a membrane and then attached to a membrane in contact with a transducer detection surface. This method avoids binding the bioprobe onto the transducer and may be desirable for large-scale production. Membranes particularly suitable for this application include nitrocellulose membrane (e.g. from BioRad, Hercules, Calif.) or polyvinylidene difluoride (PVDF) (BioRad, Hercules, Calif.) or nylon membrane (Zeta-Probe, BioRad) or polystyrene base substrates (DNA.BIND™ Costar, Cambridge, Mass.).

Development of an Integrated Circuit Microchip (ICM)

ICM System and Design

An important component of an ICM is the detection method and spectral range of sensing system. In the present work, several optical detection systems based on fluorescence of visible and near-infrared (NIR) dyes have been investigated for non-radioactive detection of tagged gene probes. Fluorescence detection means employing the integrated microchips of the present invention have been shown to selectively detect hybridized nucleic acids bound to the chip.. As shown previously, zeptomole ($10^{-21}$ mole) detection limit using fluorescence detection of dyes with laser excitation is possible (Vo-Dinh et al., 1994). The miniaturization of optical biosensors is facilitated by the versatility of waveguide configurations. FIG. 3A shows one configuration of a nucleic acid detection biochip. Various configurations and uses of the DNA biochips are illustrated in FIG. 3B.

ICM System Using Integrated Phototransistors

The instrumental system discussed herein includes the design of integrated electrooptic sensing photodetectors for the biosensor microchips. Highly integrated biosensors are made possible partly through the capability of fabricating multiple optical sensing elements and microelectronics on a single integrated circuit (IC).

FIG. 3A, FIG. 3B, and FIG. 4A show an example of such integration. This figure schematically shows a two-dimensional array of optical detector-amplifiers integrated on a single IC chip. The insert in this figure shows that each optical detector is a phototransistor coupled to a transimpedence amplifier followed by an amplifier. This block is repeated several times on the IC chip and combined with other electronic elements such as filters and amplifiers, which can also be integrated on the same IC.

The operational amplifier used with the phototransistor is a two-stage, unbuffered amplifier. The circuit is compact, occupying an area of only 185 $\mu$m×200 $\mu$m, yet has moderately high performance. It was designed to be useful for wide-band amplification and low-level signals. The gain-bandwidth product is 70 Mhz and the amplifier is stable for gains greater than 10. Other typical characteristics include: input offset voltage less than 5 mV, DC gain of 220, positive slew rate of 80 V/$\mu$s and negative slew rate of 9V/$\mu$s. The circuit requires 2.5 mW from a single 5-V supply. In the preferred embodiment this IC chip performed the complete conversion from an optical signal to an electrical signal suitable for data digitization and capture by a computer.

FIG. 4B shows the physical layout of the phototransistor and amplifier circuit. The circuit was fabricated in a 2-$\mu$m, p-well CMOS process and occupied an area of 160,000 square microns. The phototransistor is composed of 220 phototransistor cells connected in parallel. An individual phototransistor cell occupied 760 square microns. The transimpedence amplifier had a gain of 100 kV/A. As the phototransistors were coupled with the 10-fold amplifier gain, the resulting gain was $10^6$ V/A. The phototransistors had a conversion gain on the order of 10 $\mu$A/$\mu$W, so the entire chain had an approximate conversion gain of 10 V/$\mu$W. The exact gain generally depends on the spectral region of interest and, to some extent, on the signal level being monitored.

The above described elements may be modified to tailor the devices to specific applications. Since the phototransistor is made from basic photocell elements, it can be connected to as many cells as needed to create the desired geometry or required number of channels to adapt the detector to a specific application. Similarly, the gain and bandwidth of the amplifiers can be adjusted using simple resistor or capacitor changes as the application requires. Other light sensing structures in addition to the phototransistor may be fabricated using standard Complementary Metal Oxide Semiconductor (CMOS) processing steps. Several photodiode structures are possible using the p-n junctions that would ordinarily form wells or transistors.

ICM System with Integrated Phototransistors

Figure 3:
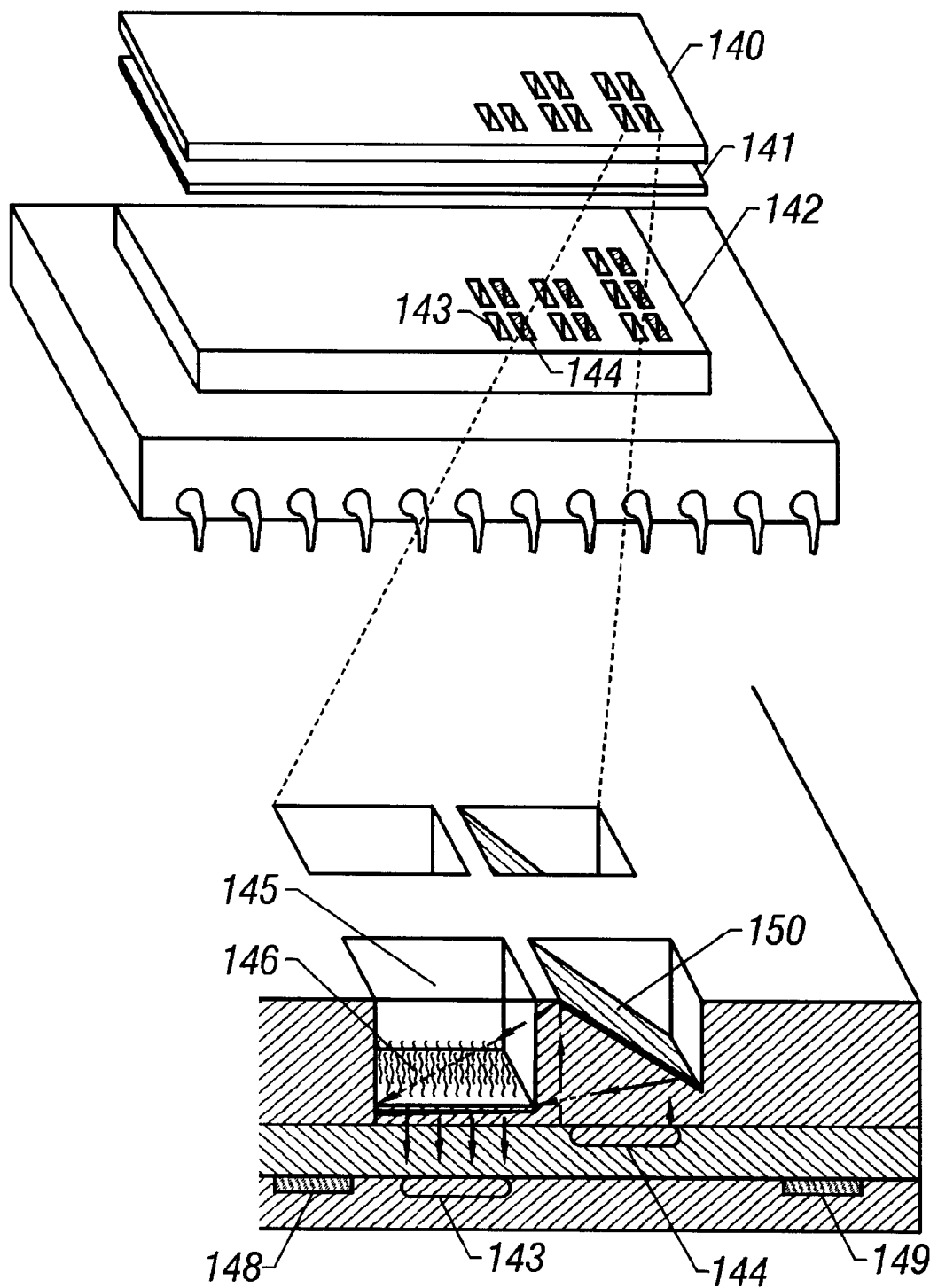
FIG. 3 is a perspective, partially enlarged and exploded schematic view of a biochip having multiple arrays of exciting light sources and detectors.
Figure 4:
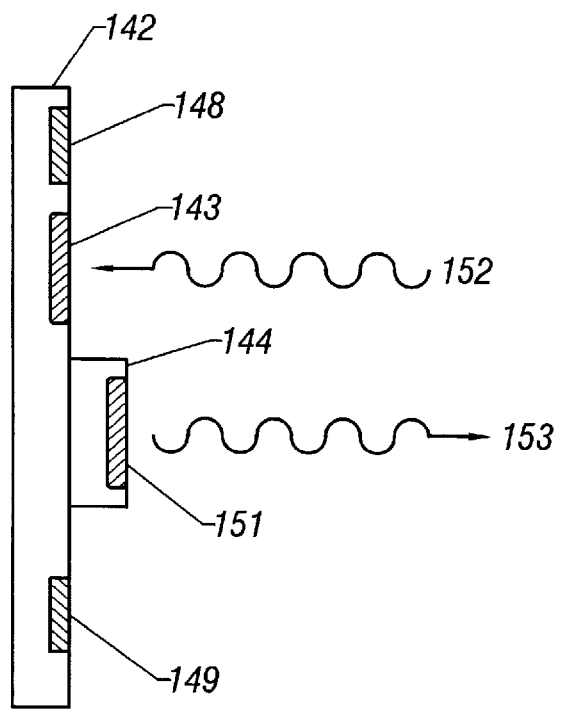
FIG. 4 is a schematic, sectional view of an integrated circuit microchip system for a biochip with integrated light emitting diode excitation sources.
Figure 5:
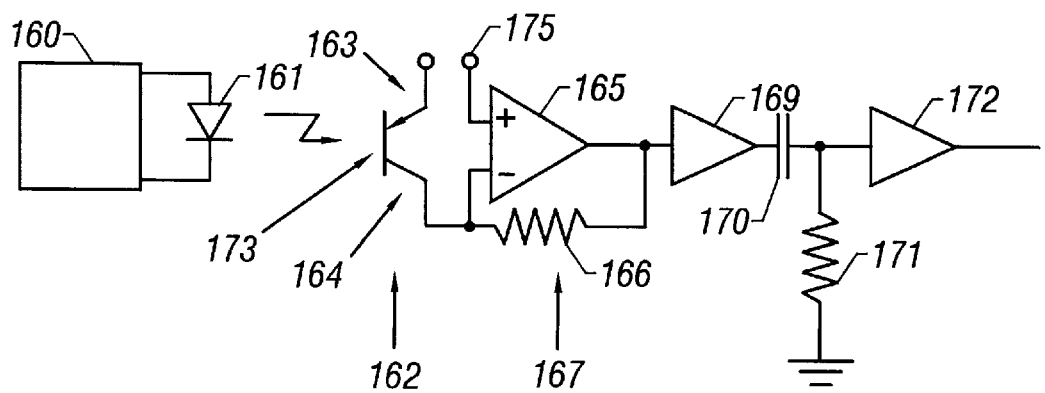
FIG. 5 illustrates a schematic circuit diagram for an integrated light emitting diode (LED) light source and phototransistor detection device.
Figure 6:
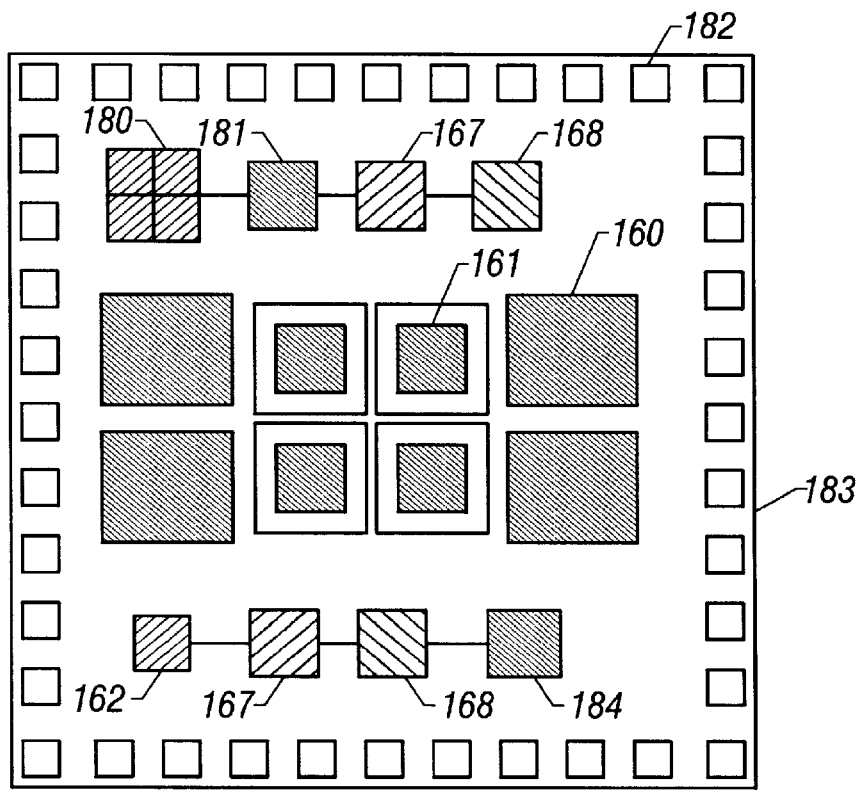
FIG. 6 illustrates a schematic layout of an integrated circuit that implements the light source and detection device illustrated in FIG. 5.

A biochip having multiple arrays of exciting light sources and detectors is shown in FIG. 3. A design of an ICM system for such a biochip with integrated light emitting diodes (LED) excitation sources is illustrated in FIG. 4. This ICM system contains both GaAs chips used as light sources and the phototransistor as the detector. The electrooptic circuit and layout of this device shown in FIG. 5 and FIG. 6 FIG. 5 and FIG. 6 show the schematic diagram of the IC circuit and layout for the IR light source and the analog signal detection, respectively.

ICM System with 4×4 N-Well Photodiode Array

A second ICM system includes large-area, 4×4 n-well integrated amplifier-photodiode array that has been designed as a single, custom integrated circuit (IC), fabricated for the biochip. This IC device is coupled to the biosensor and is designed for monitoring very low light levels.

Figure 7:
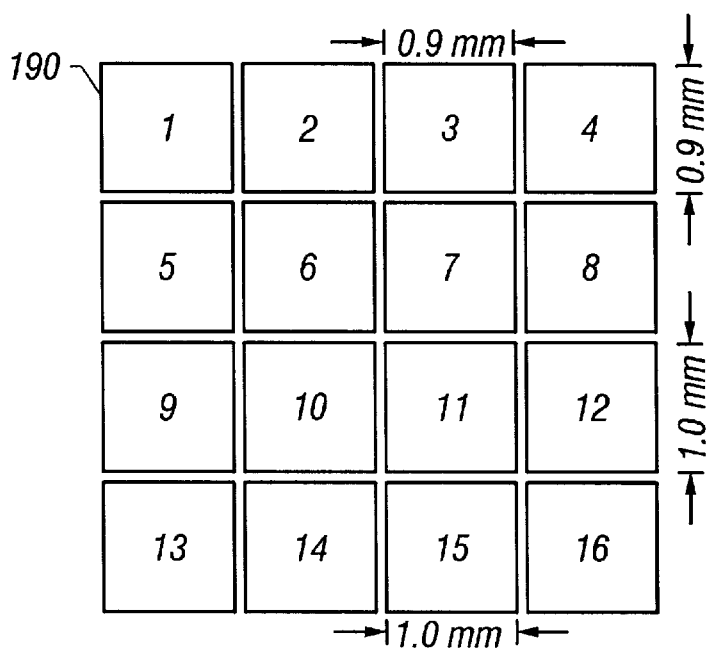
FIG. 7 illustrates a physical layout of a large-area, 4×4 n-well integrated amplifier-photodiode array designed as a single, custom integrated circuit.
Figure 8:
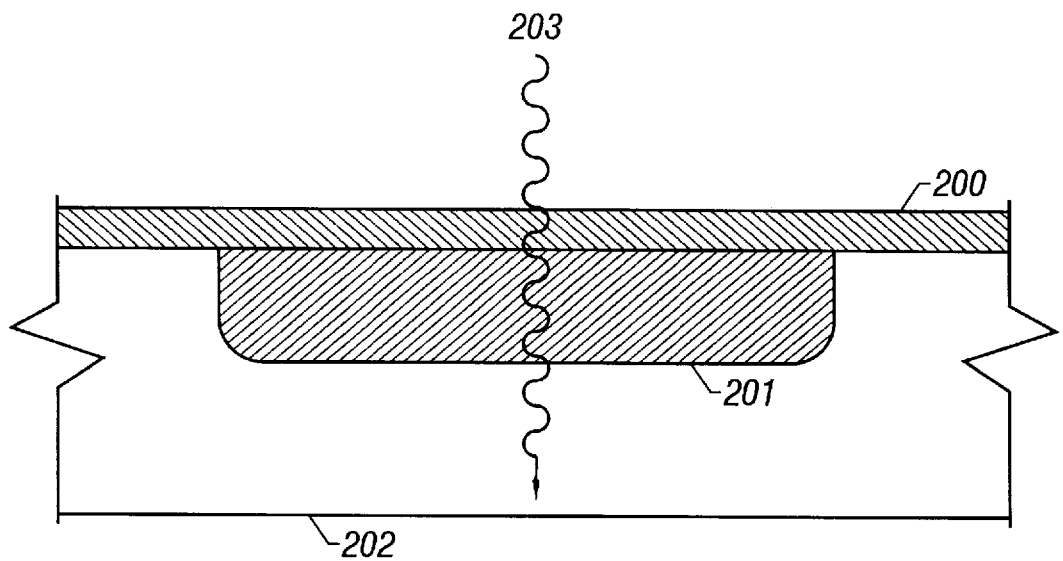
FIG. 8 illustrates a schematic cross-section of an n-well photodiode used in the photodiode array of FIG. 7.

The physical layout of the IC array is illustrated in FIG. 7 shows the individual photodiodes have 0.9-mm square size and are arrayed on a 1-mm grid. The photodiodes and the accompanying electronic circuitry were fabricated using a standard 1.2-micron n-well CMOS process from Orbit Semiconductor (Sunnyvale, Calif.). The use of this type of standard process allows the production of photodiodes, phototransistors as well as other numerous types of analog and digital circuitry in a single IC chip. The photodiodes themselves are produced using the n-well structure that is generally used to make resistors or as the body material for a PMOS transistor. FIG. 8 shows a schematic cross-sectional drawing of the n-well photodiode. Since the anode of the diode is the p-type substrate material, which is common to every circuit on the IC chip, only the cathode is available for monitoring the photocurrent and the photodiode is constrained to operate with a reverse bias.

Figure 9:
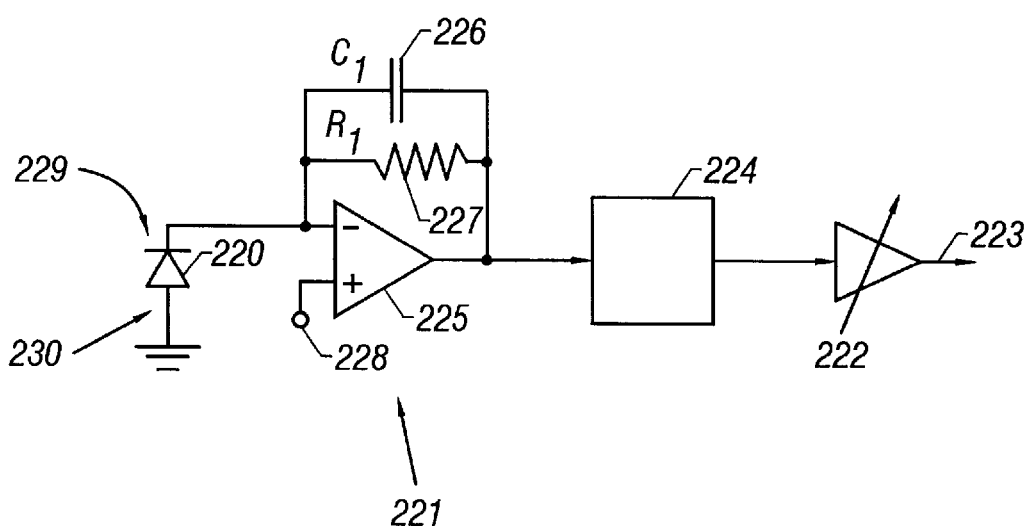
FIG. 9 illustrates a detection circuit for use in conjunction with the photodiode array of FIG. 7.

FIG. 9 shows a one-diode version of the circuit. The operational amplifier and feedback resistor $R_1$(227) form a transimpedence amplifier that is used to convert the photocurrent into a voltage. The conversion gain (V/A) is determined by the value of rasistor 227. The feedback capacitor performs two functions: (a) it prevents the amplifier circuit from oscillating, and (b) it limits the bandwidth of the circuit. Generally, the bandwidth should be no more than that necessary for the desired measurement. Reduction of the bandwidth decreases the noise present at the amplifier's output, so if this reduction can be accomplished without attenuating the signal, a net gain in signal-to-noise ratio is achieved. For this circuit, the signal bandwidth is given by $f=1/(2\pi R_1 C_1)$, where $R_1$ is the resistance and $C_1$ is the capacitance.

The voltage applied to the non-inverting input of the operational amplifier determines the reverse bias applied to the photodiode. The IC can be operated with a single %—v supply—For example, if 2 V is applied to the non-inverting input, then the dc level of the other input and the output will also be 2 V, so the reverse bias on the diode will be 2 V. Photocurrents flowing into the diode will also flow through the feedback resistor, causing the amplifier output to become more positive. As the operational amplifier output cannot exceed the positive supply, the maximum output will be approximately 5 V, so the maximum signal excursion is 3 V, which corresponds to a maximum current of 3 V/R1.

Figure 10:
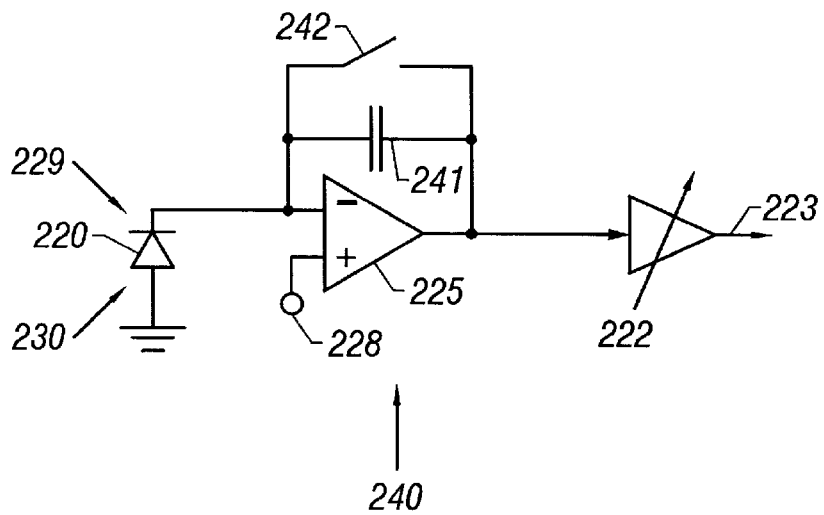
FIG. 10 illustrates an alternative detection circuit for use in conjunction with the photodiode array of FIG. 7.

Alternative photodiode and integrated amplifier circuit block diagrams are shown in FIG. 10. Alternate to the transimpedence amplifier plus low-pass filter readout method is the use of an integrating amplifier as shown in FIG. 10. In this case, the amplifier integrates the current from the photodiode until the signal is converted to digital format. After conversion, the integrator is reset to its initial state and is capable of starting another measurement. This scheme has the advantage that the integration time can be controlled to allow adapting to various light (and therefore current) levels. The disadvantage of this scheme is that it requires coordination between the analog-to-digital conversion process and the integrator.

Figure 11:
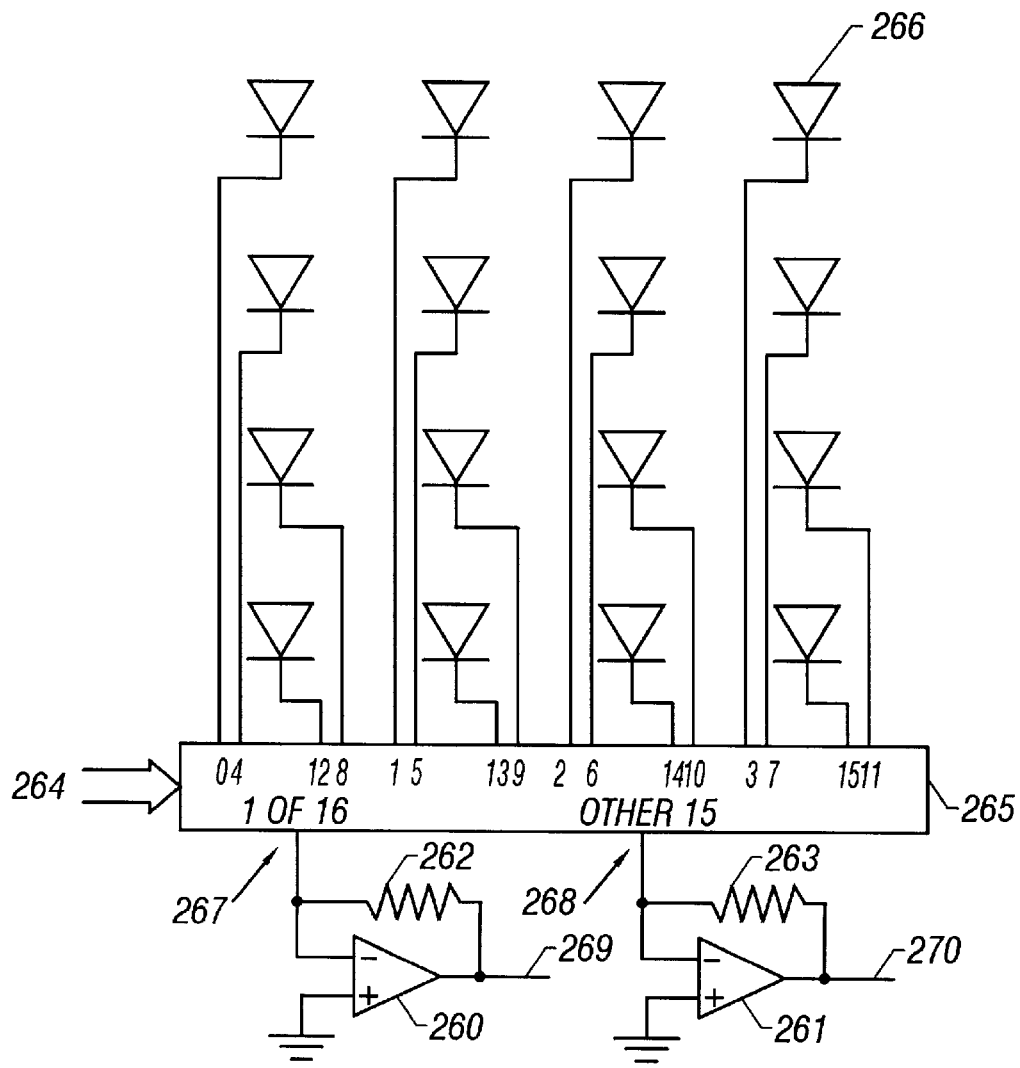
FIG. 11 illustrates schematically an analog multiplexer that enables any element in the photodiode array of FIG. 7 to be connected to an amplifier.
Figure 12:
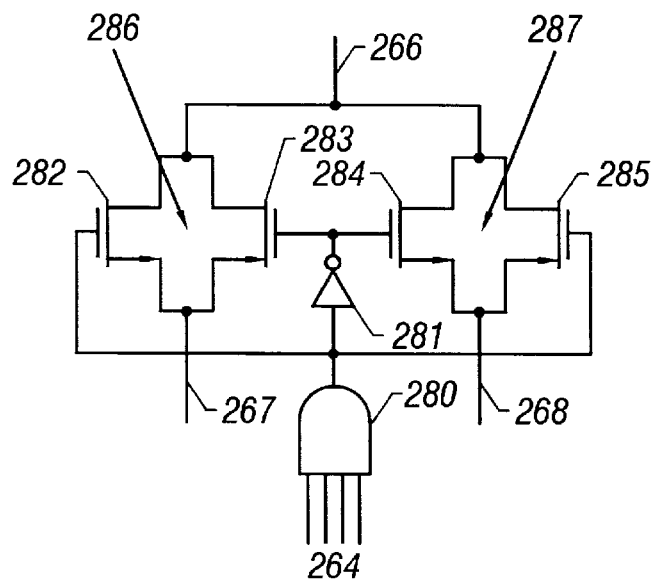
FIG. 12 illustrates one possible schematic implementation of the multiplexer in FIG. 11 for use with 16 cells.

An analog multiplexer is designed to allow any of the elements in the array to be connected to an amplifier. In a specific embodiment, each photodiode could be supplied with its own amplifier. For this many applications, this feature is not necessary unless the additional data acquisition speed due to having parallel channels is required. The multiplexer is made from 16 cells as illustrated in FIG. 11. Each cell has two CMOS switches that are controlled by the output of the address decoder cell. Each cell has a unique 4-bit address. One switch is closed only when that particular cell is the one that is being addressed while the other switch is closed, except when that cell is the one being addressed. This process connects the addressed diode to one amplifier while all the others are connected in parallel to the other amplifier as shown in FIG. 12.

This arrangement allows connecting a 4×4 array of light sources (different fluorescent probes, for example) to the photodiode array and reading out the signal levels sequentially. With some modification, a parallel reading system can be designed. Using a single photodiode detector would require mechanical motion to scan the source array. The additional switches and amplifier serve to correctly bias and capture the charge generated by the other photodiodes. Failure to do this would result in erroneous measurements due to the addressed photodiode collecting current generated from elsewhere in the IC. Additionally, the additional amplifier and switches allow using the IC as a single, large area (nearly 4 mm square) photodetector.

Alternative Photodetectors

An avalanche photodiode (APD) provides an alternative solid-state method of detecting low light levels. Advantages of APD arrays over ordinarily used photodiode arrays include electron multiplication obtained by the avalanche process. This may improve the signal-to-noise ratio so that lower light levels are detected.

The process of making an APD and/or APD arrays from silicon includes fabricating structures that are not compatible with steps used in standard CMOS processing. A fully integrated microchip including avalanche photodiodes requires special semiconductor fabricating processes. Such processes are known in the art (Geiger, et al., 1990 and Aubert, et al., 1988).

Alternate Photodiode Array Readout Schemes

There are several alternate possibilities for reading out an array of photodiodes in addition to the multiplexed scheme that was implemented. For many applications, the low pass filter time constant is set to a large value to improve the signal-to-noise ratio. This requires a long time to acquire data for the whole array if each diode is read sequentially. For example, if the time constant is set to 1 second and the array is 4×4, then the minimum time to acquire data would be something 4×4×1 second×5=80 seconds. The last factor of 5 allows for the amplifier and low pass filter to settle to better than 1% accuracy after its input is switched to another photodiode.

Figure 13:
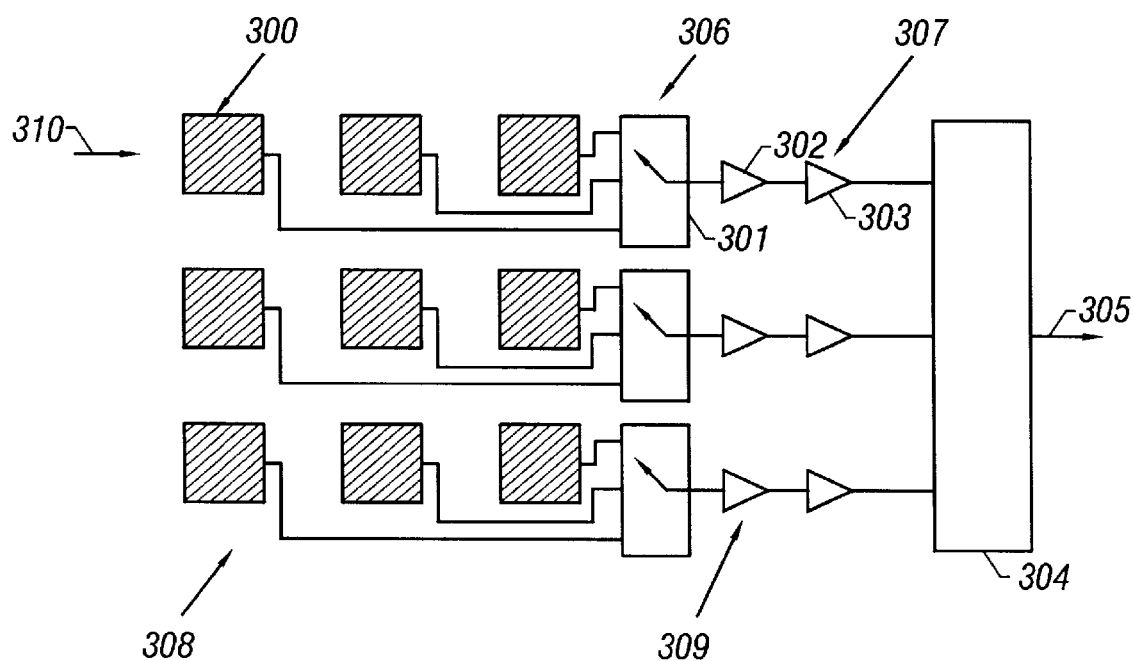
FIG. 13 illustrates schematically a partially-parallel system that may be used to obtain data from the photodiode array shown in FIG. 7. The partially-parallel system has only a readout system for every row of photodetectors.

Partially Parallel Readout Scheme. According to one embodiment of the invention, the row of diodes are multiplexed into one amplifier/low pass filter circuit. Columns or other subunits of the array could be used as well. The output of each filter is input to a multi-channel analog-to-digital converter (ADC), which can be implemented on the same IC as the photodiode array, amplifier and filter. Compared to the sequential or serial readout case, the time required is reduced by a factor of n for an n×n array. The schematic block diagram of this partially parallel readout system is shown in FIG. 13.

Figure 14:
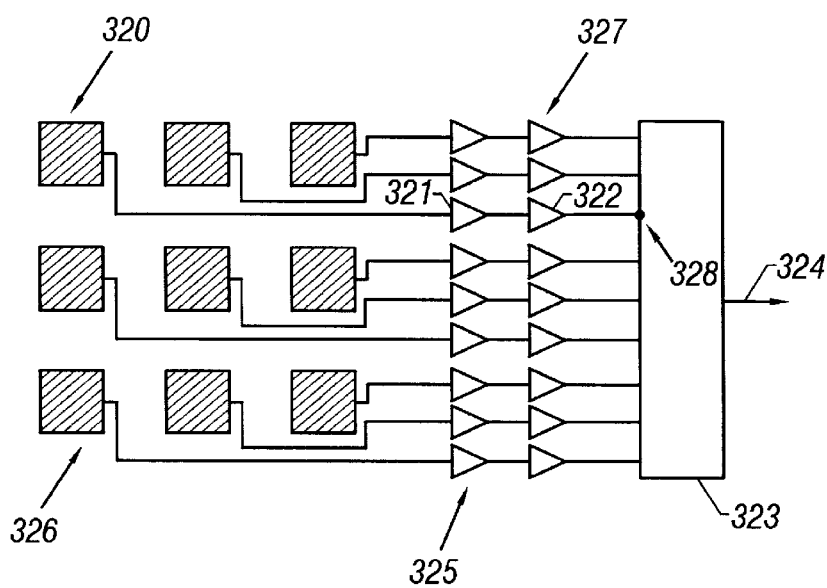
FIG. 14 illustrates a fully-parallel system that may be used to obtain data from the photodiode array shown in FIG. 7. The fully-parallel device has a read-out system (amplifier, electronics) for every photodetector.

Fully Parallel Readout Scheme. This provides the fastest readout speed. Each diode is provided with its own amplifier, low-pass filter and ADC input channel. Compared to the serial readout case, the time required is reduced by a factor of $n^2$ for an n×n array. The block diagram at a fully parallel readout system is shown in FIG. 14.

Photodetector Array Sizes

One advantage of a custom biosensor IC is that the photodiodes can be made to physically match the probe. The prototype uses 0.9-mm square photodiodes on a 1 mm×1 mm square grid, but arrays with a larger number of smaller photodiodes can be made. Using readily available 1.2-micron technology, photodiodes on a 20-micron grid could be made for a 10×10 array. This would give 100 photodiodes in an area only 0.04 $mm^2$, i.e. 2500 photodiodes per $mm^2$. Even more density is possible using 0.5-micron processes that are commercially available.

Using the serial readout scheme allows most of the chip area to be used for the photodiode array. It is likely that a 1000 element array will fit on a 5 mm×6 min IC, which would be considered a medium-sized die format. For large arrays using the fully parallel readout scheme, the limiting factor on IC area is most likely the area required by the wiring and the readout electronics. Future advances in IC technology could increase the density of elements on the chip.

The partially parallel readout scheme is a compromise between the other two cases. Compared with the serial case for a large array, the die size might double to allow partially parallel readout.

Alternative Detection Circuits

Previous examples have shown use of a transimpedence amplifier to convert the current to a voltage and low-pass filters to improve signal-to-noise ratio for very low frequency or dc signals. Such filters may be implemented as digital filters or for different types of signals, such as a fluorescence or phosphorescence decay. A filter matched to the signal could be used to give optimal identification of the signal.

In another embodiment according to the invention, present low current levels may also be measured by other means such as integrating the current for a fixed time prior to measuring the voltage. Alternatively, one may integrate the current until a predetermined voltage level is reached and measure the time required for the integration. These methods use the following relations allowing the determination of current from measured voltages, capacitances and times.

charge=current×time charge (on a capacitor)=capacitance×voltage

The circuit used to integrate current is similar to the transimpedence amplifier shown in FIG. 9, except that the feedback element of the amplifier is a capacitor shown as 241 in FIG. 10 instead of a resistor.

Another integrating amplifier possibility is to make an amplifier that amplifies the voltage developed across a capacitor which receives the charge.

In yet another embodiment according to the present invention, another method of using an integrating amplifier is to employ an oscillator. The integrator integrates the unknown current to a preset voltage and then is reset by discharging the capacitor with a switch and the integrator is allowed to start again. This then cycles repeatedly. The frequency of oscillation is proportional to the input current. This common technique in circuit design may be used in the systems disclosed herein.

Several methods may be employed to implement the integrating capacitor for the described detection circuits. One may use a capacitor such as polysilicon that is compatible with CMOS technology. Or one may take advantage of the capacitance of the photodiode itself, using the amplifier to amplify the voltage across the photodiode. This has the advantage that fewer components are needed compared to using separate integrating capacitors. For an array of photodiodes, all photodiodes may be integrated simultaneously and one (fast) amplifier used to multiplex the outputs without depriving the circuit of significant measurement time.

Excitation Light Sources

Light sources such as light-emitting diodes (LEDs) and semiconductor lasers may be used in connection with the integrated microchips herein described. One may also choose to employ alternative microlaser systems such as edge-emitting lasers and surface emitting lasers. Vertical-cavity surface-emitting (VCSELs) are particularly suitable light sources for integrated microchips. The linearity of laser arrays makes them ideal for compact 2-dimensional and 3-dimensional configurations in ICM systems. Quantum Cavity (CQ) lasers can also be used due to their small sizes. The QC lasers provide powerful mid-infrared semiconductor lasers that can be used in absorption and Raman mode.

Figure 29:
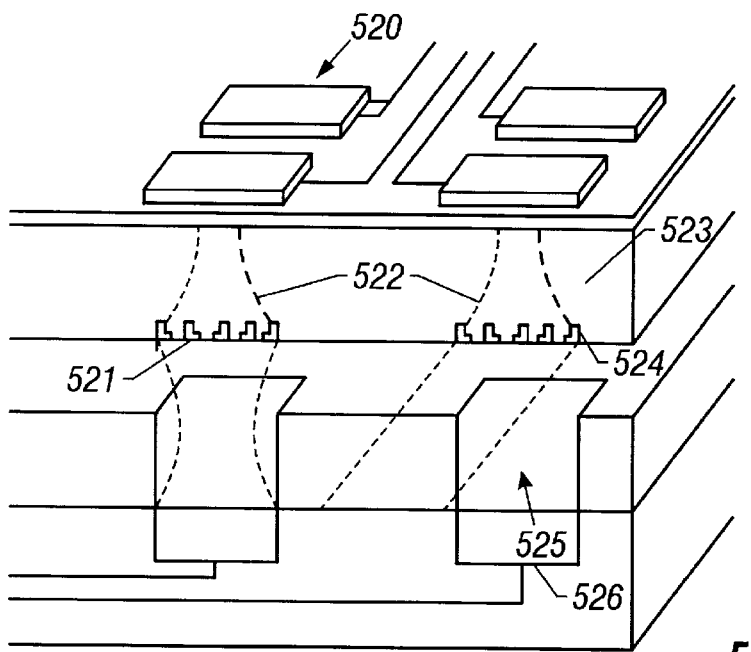
FIG. 29 illustrates an embodiment of the present invention that uses individually addressable, integrated vertical-cavity surface-emitting lasers (VCSEL) and on-axis and/or off-axis diffractive lenses.

The ability to shape the diverging beam from a surface-emitting laser or a light-emitting diode is important for micro-optic illumination in ICM systems. One may use diffractive optical elements (DOE) systems that can be integrated into the ICBM devices. For example, a wide variety of optical elements may be designed and fabricated using current processing technologies. Compact DOEs and VCSELs can be integrated and fabricated on a single transparent substrate as illustrated in FIG. 29. The DOEs can be etched directly into the substrate. Such a compact source-diffractive lens is ideal for miniature optical ICM array design.

Evaluation of Visible and NIR Dye Labels for Gene Probes

Many photodetectors used in IC chips operate in the red and near infrared (NIR) spectral region. It is therefore important to develop and evaluate DNA labels in the red and NIR region. The inventors have investigated gene probe sensing methods using both visible (350–700 nm) and NIR (700–1000 nm) spectral range fluorescent dye labels. Excitation and detection in the NIR range presents certain difficulties but also offers several advantages. Measurements in the NIR have less background fluorescence interference since very few species with NIR emission occur in samples such as sea water, tissue, serum and other body fluids. Since the intensity of scattered light exhibits frequency$^4$ (fourth-power) dependence, samples that appear opaque in the visible region may be more transparent in the NIR region. Finally, an important advantage associated with NIR measurements is the availability of low-cost, miniaturized diode lasers which usually have emission lines in the red and NIR regions.

Figure 15:
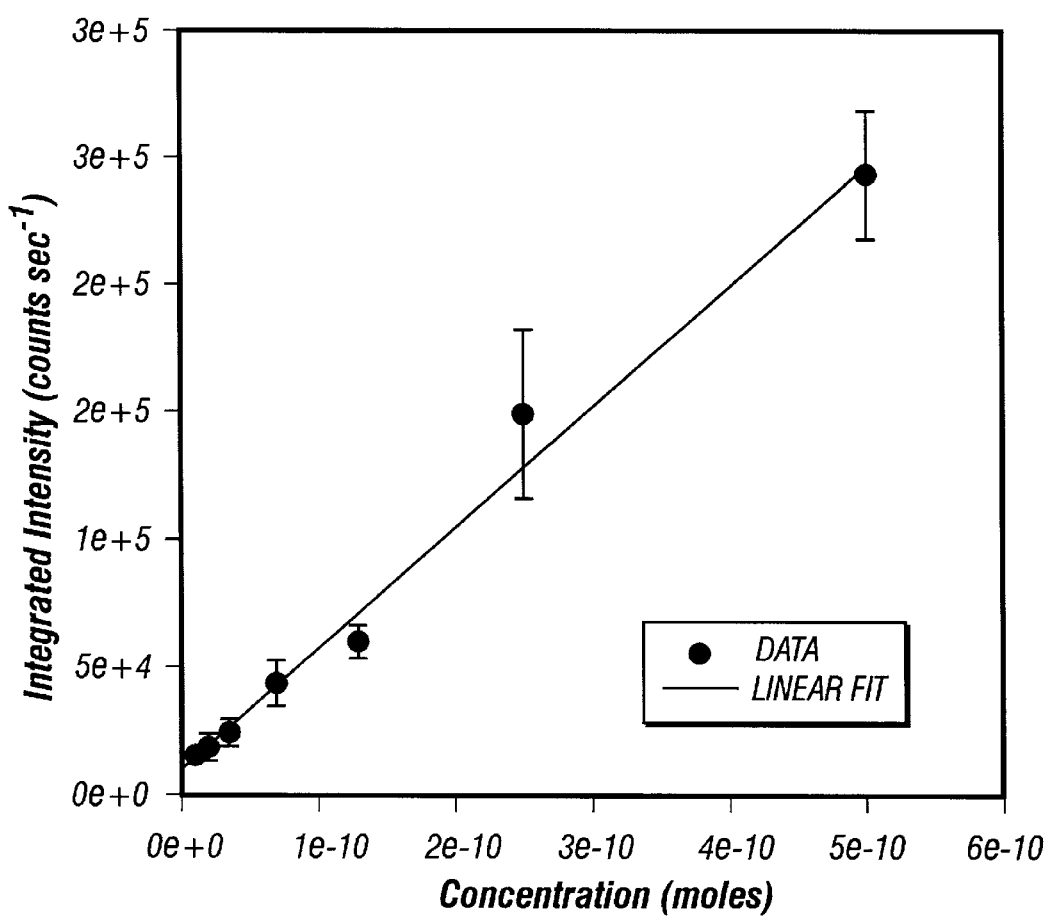
FIG. 15 shows a calibration curve for an NIR dye-labeled single-stranded DNA (sequence: 5'-CCTCCTCCTTCCCAGCAGGG-3'; SEQ ID NO:1) over a concentration range from 1 pmol/μL to 3 fmol/μL.

Thus, NIR dye labels in gene probe biosensors offer the advantages mentioned. In one model example, a waveguide multiprobe system with CCD detector configuration was used. The diode laser line of 780 nm at 9.5 mW was used for excitation. FIG. 15 shows a calibration curve for a NIR dye-labeled single-stranded DNA (sequence: 5'-CCTCCTCCTrCCCAGCAGGG-3'; SEQ ID NO:2) over a concentration range from 1 pmol/$\mu$L to 3 fmol/$\mu$L. Excitation light was provided by a pen-size 9.5-mW laser diode (780 nm) and measurement times ranged from 1 to 3 min. This calibration curve was linear over the full range of the dye concentration investigated. The limit of optical detection, based on a signal equal to three times the standard deviation of the noise, was estimated to be in the 100 attomole/$\mu$L.

Figure 16:
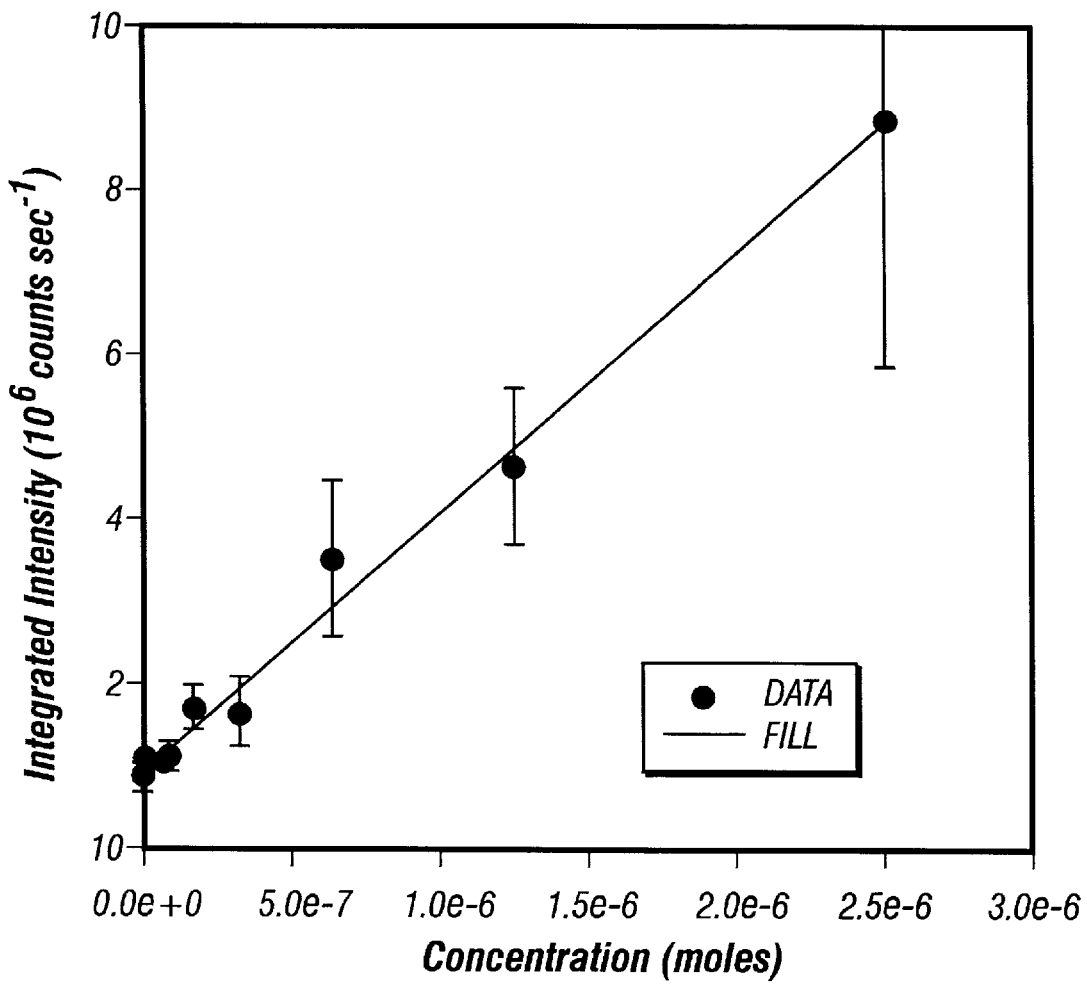
FIG. 16 illustrates the results of measurements of gene probes tagged with fluorescein, a dye label emitting in the visible range.

FIG. 16 shows the results of measurements of gene probes tagged with fluorescein, a dye label emitting in the visible range. Measurement times ranged from 0.05 to 2 s. The results show that the calibration curve is linear even with concentrations as low as approximately 2 nmol/μl. The higher detection limit is attributed to an increase in background fluorescence of the waveguide in the visible region.

Evaluation of the ICM Biosensor Systems

Figure 17:
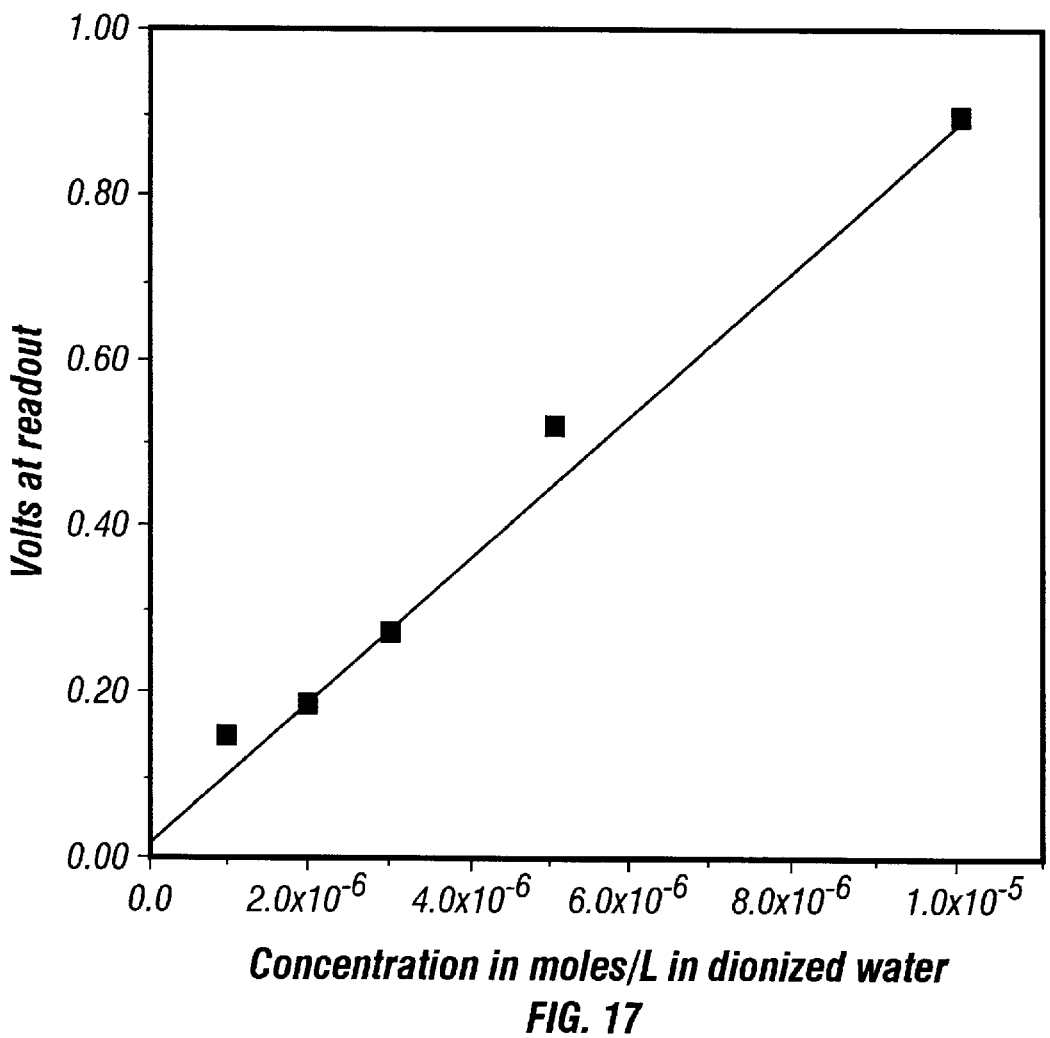
FIG. 17 illustrates the performance of an integrated circuit microchip (ICM) phototransistor and amplifier circuit consisting of a 2 μm, p-well CMOS process occupying an area of 160,000 square microns and 220 phototransistor cells connected in parallel by showing the signal output response for various concentrations of the dye label Rhodamine-6G excited with a small helium-cadmium laser (8 mW, 325 nm).

The microchips designed and fabricated for this study were evaluated by measuring the fluorescence signal of a fluorescent dye spotted onto the detector. FIG. 17 shows the performance of the specially designed ICM phototransistor and amplifier circuit (device No. ICI N551-CD2) which consisted of a 2-μm, p-well CMOS process and occupied an area of 160,000 square microns. As described in the experimental section, the phototransistor was actually composed of 220 phototransistor cells connected in parallel. The figure shows the signal output response for various concentration of the dye label Rhodamine-6G excited with a small helium-cadmium laser (8 mW, 325 nm). The results illustrate the linearity of the microchip detector with respect to the label concentration.

Measurements using an amplifier-phototransistor (APT) ICM device with 4×4 array of phototransistors (FIG. 18) have been performed. The photocurrent of each channel of the APT microchip was recorded using a digital photometer. The data from the photometer were transferred to a personal computer (PC) via an RS-232 link. The samples consisted of an array of microspots of fluorescein-labeled DNA on a membrane. The membrane was placed on a glass slide connected to a linear translation stage. The measurements were made while the translation stage moved the sample arrays over the stationary phototransistor device. Light from an argon ion laser at 488 nm was transmitted via an optical fiber and focused onto a sample spot. An appropriate optical filter placed between the sample substrate and the detector array was used to reject the laser radiation.

Figure 19:
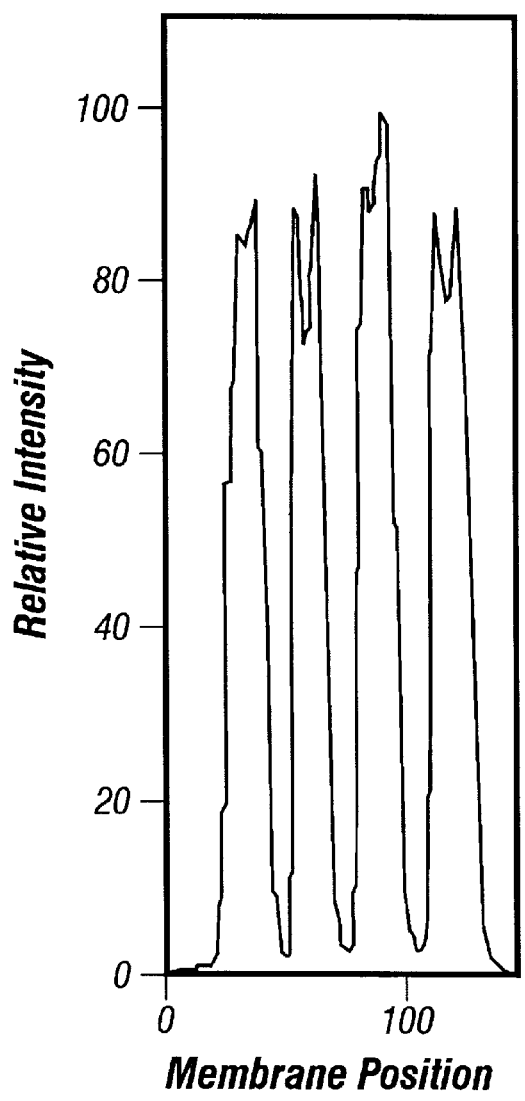
FIG. 19 illustrates the results when four sample spots of 1 μL of fluorescein labeled DNA were placed on a nitrocellulose membrane that was translated over a detection channel of the device shown in FIG. 18.
Figure 20:
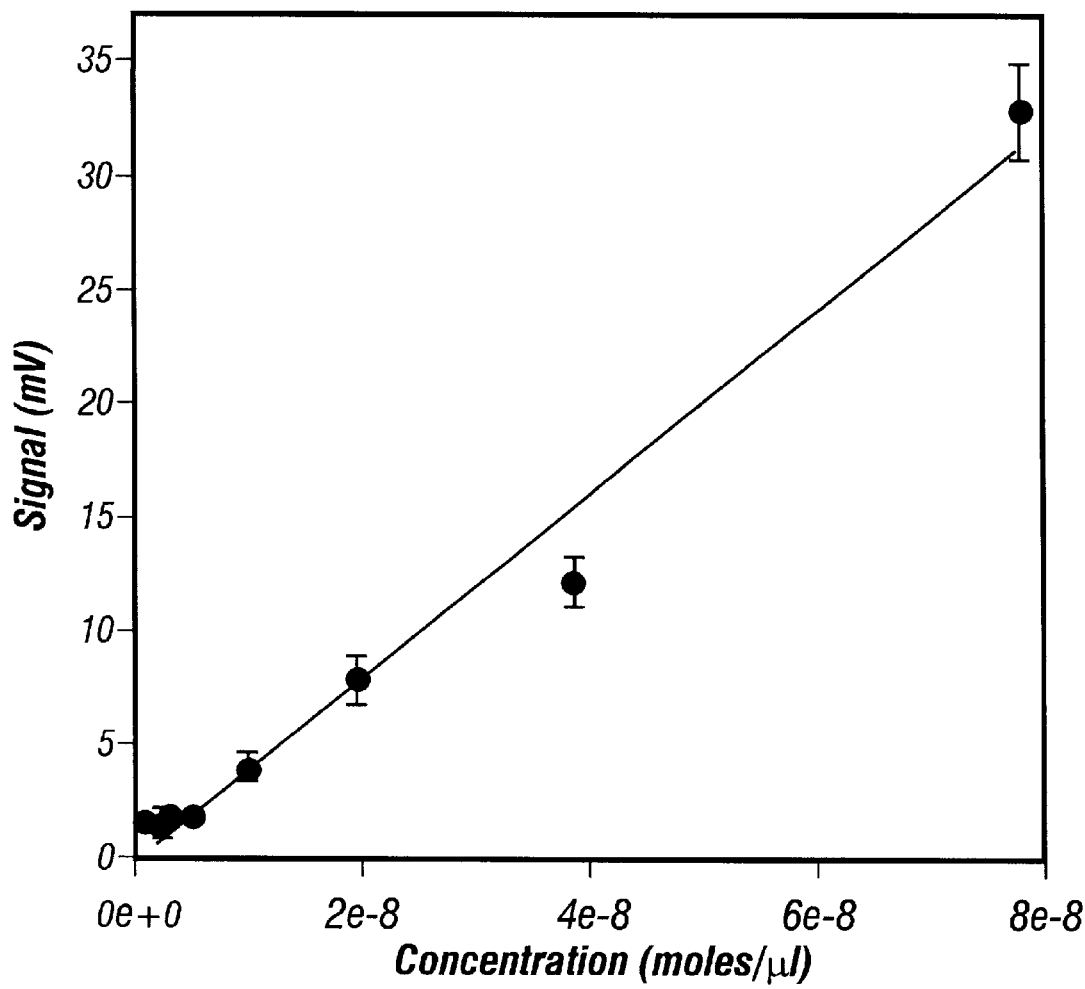
FIG. 20 illustrates the calibration curve of fluorescein labeled DNA using the device shown in FIG. 18.

The data obtained with this experimental set up showed four resolved signals as the sample spots moved over an APT microchip channel (FIG. 19). Four sample spots of 1-μL of fluorescein-labeled DNA probes were placed on a nitrocellulose membrane, which was translated over a detection channel of an AP-ICM biochip. As the DNA spot passed over the photodetector, a fluorescence signal is detected. The 4 peaks in FIG. 19 illustrate the detection of the 4 DNA spots on the substrate by the ICM device. FIG. 20 shows the calibration curve of the fluorescein-labeled DNA using the APT microchip device. This demonstrates the possibility for quantitative measurements of the microchip device.

The photodiode array (PDA) microchip device using photodiode array was also evaluated and showed excellent sensitivity with the NIR dye labeled DNA. The results demonstrate the feasibility of the ICM technology for used in DNA biosensor applications.

EXAMPLES

The following examples are included to demonstrate preferred embodiments of the invention. It should be appreciated by those of skill in the art that the techniques disclosed in the examples which follow represent techniques discovered by the inventors to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Preferred embodiments of the present invention are illustrated in FIGS. 1–29 of the drawings, like numerals being used to refer to like and corresponding parts of the various drawings.

Example 1

Nucleic Acid Biochip Integrated Device

FIG. 1 shows an exploded, schematic, perspective view of an example of DNA biochip 109 that combines optical and electrical components. The components shown include a light source 101, optical element 102, filter 103, reflective optic 104, sampling platform 105 for receiving and delivering sample 110 onto spot arrays 106 on a substrate 111, filter 107, and an array of photodetectors 108.

The optical elements shown in FIG. 1 may be positioned separately from the biochip 109, but are preferably integral with the biochip. In the latter instance, a transparent shield or seal (e.g. plate made with glass or quartz or plastic which is optically transparent at the wavelengths of interest for detetion) isolates the optical component from the biochemical components. Light from light source 101 travels through self-imaging optical element 102 (e.g. defractive optics, binary optics or self-imaging optics systems that transform a point source into 2-dimensional array of light beams) and filter 103 to select and spectrally isolate the incident wavelength and is reflected by reflective optic 104 onto the sample platform 105. A signal from a hybridization event passes through filter 107, which blocks the light from the light source 101, and is detected by the phototransistor array 108.

Example 2

Optical Detector and Amplifier Circuit

Figure 2:
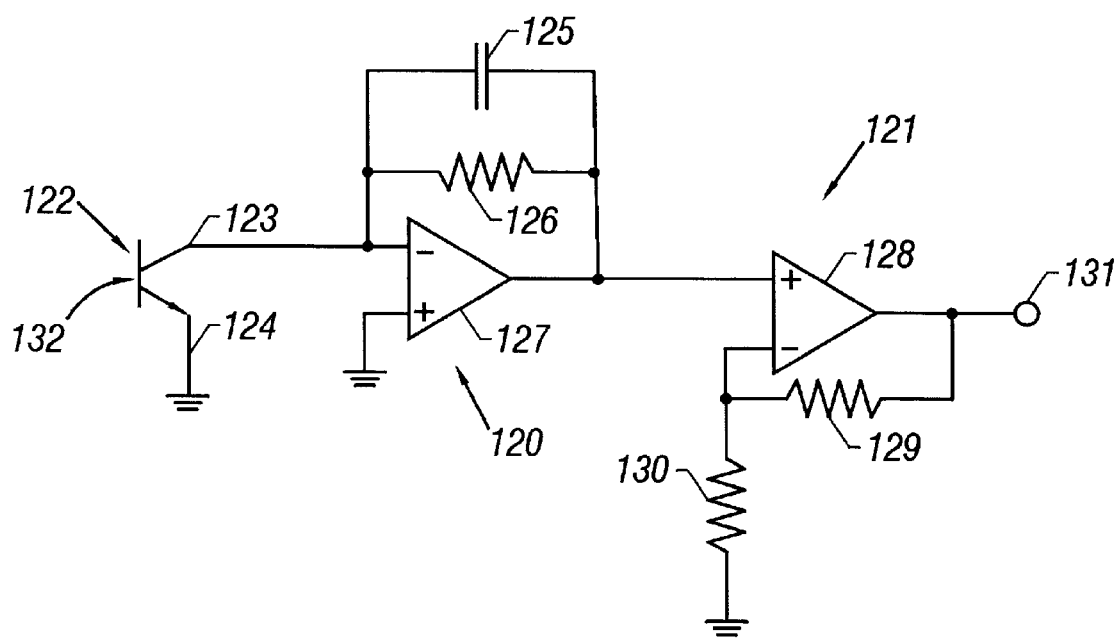
FIG. 2 illustrates a schematic diagram of one possible optical detector and amplifier circuit that may be implemented on an integrated circuit in order to convert an optical signal into an electrical signal suitable for data digitization and capture by a computer.

These optical detector and amplifier circuit shown in FIG. 2 may be implemented on an integrated circuit in order to convert an optical signal into an electrical signal suitable for data digitization and capture by a computer. The optical detector and amplifier includes a phototransistor 122 coupled to a transimpedence amplifier 120, which converts a current signal into a voltage signal and which is followed by an amplifier 121. The operational amplifier 127 in the transimpedence amplifier 120 is a two-stage, unbuffered amplifier.

In one embodiment, capacitor 125 has a value of 2 pF and resistor 126 has a value of 100 KΩ. The gain of amplifier 121 is equal to 1+(Resistance 129/Resistance 130). Thus, in one specific embodiment for which the gain of amplifier 121 is 10, resistors 129 and 130 are chosen so that their ratio is 9. The circuit is compact (185 μm×200 μm), but has moderately high performance. It is designed to be useful for wide-band amplification and low-level signals. The gain-bandwidth product is 70 MHz, and the amplifier is stable for gains greater than 10. In addition, the circuit has an input offset voltage less than 5 mV, a DC gain of 220, a positive slew rate of 80 V/μs, and a negative slew rate of 9 V/μs. The circuit requires 2.5 mW from a single 5 V supply. The circuit of FIG. 2 may be fabricated in a 2 μm, P-well CMOS process.

In one embodiment of such a circuit, phototransistor 122 is composed of 220 phototransistor cells that are connected in parallel. Each phototransistor cell occupies an area of 760 square microns, and the entire circuit occupies an area of 160,000 square microns. The transimpedence amplifier has a gain of 100 kV/A and is followed by an amplifier with a gain of 10. Thus, the total gain is $10^6$ V/A. The phototransistors have a conversion gain on the order of 10 μA/μW, and thus the entire circuit has an approximate conversion gain of 10 V/μW. The exact gain generally depends on the spectral region of interest and, to some extent, on the level of the signal being monitored.

The circuit described by FIG. 2 may be modified as required by specific applications. Since the phototransistor cell 122 is composed of basic photocell elements, it may be connected to as many cells as needed to create a desired geometry or a required number of channels needed to adapt the detector to a specific application. Other light sensing structures in addition to the phototransistor may be fabricated using standard CMOS processing steps. Several photodiode structures are possible using standard pn junctions.

An avalanche diode is an alternative solid-state device that is capable of detecting very low light levels. An advantage it has over an ordinary photodiode is the electron multiplication obtained by the avalanche process, which results in an improvement in the signal to noise ratio that enables smaller light levels to be detected. A disadvantage of this approach is that avalanche diodes require steps and structures that are not compatible with standard CMOS processing. A fully integrated microchip including avalanche photodiodes would require the development of a special semiconductor fabrication process. An APD differs from an ordinary photodiode in that the applied reverse bias is sufficient to cause electron multiplication. The most reliable way to cause this multiplication is by a large voltage (70–500V) to deplete a p-n junction where both the p- and n-type material is lightly doped. This results in a thick region of depleted material where the electric field is high enough to produce considerable electron multiplication, but not cause electrical breakdown. The applied voltage sets the gain (electron multiplication). In a standard low-voltage IC process, the doping levels are higher and breakdown voltages are lower. Voltages sufficient to cause considerable electron multiplication are too near the breakdown voltage to allow practical APDs. However, in a "high-voltage" process (50–100V breakdown) such as those used for some industrial electronics, it might be possible to fabricate a p-n junction that could be used as an APD while still allowing standard electronics to exist on the same IC. It might be necessary to add additional diffusion steps to the process to create the p-n junction for the APD while the standard process steps would be used to create signal processing electronics.

Example 3

Biochip

Figure 30:
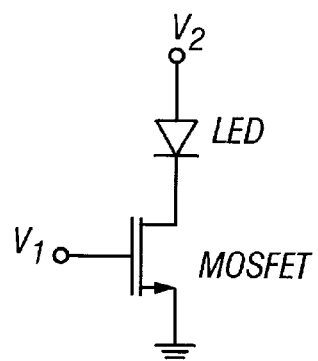
FIG. 30 is an LED driver circuit where $V_1$ is a DC voltage (5V, for example) and $V_2$ is a DC voltage (5V to turn on LED and 0V to turn off LED) or a pulse train with 5V levels turning on the LED and 0V turning off the LED.

FIG. 3 shows a biochip having multiple arrays of exciting light sources and detectors. The biochip includes a sampling stage layer 140, a filter and lens stage layer 141, and a silicon die stage layer 142. Light from light source 144 driven by a driver circuit 149, see FIG. 30, is reflected from mirror coating 150. The mirror surface is designated such that the light beam from 144 is focused and directed to cover the area of the microchamber surface which contain the DNA probe or DNA sample. If luminescence is the signal being detected, the resulting light travels through an optional filter and lens stage 147 and is detected by the photodetector 143 and the associated signal processing electronics 148 such as the system shown in FIG. 9.

Example 4

Biochip II

FIG. 4 shows a design of an integrated circuit microchip (ICM) system for a biochip as shown in FIG. 3 with substrate 142 and integrated light emitting diode excitation sources 144. This ICM system contains both a Gallium Arsenide (GaAs) chip 151 used as a light source and a phototransistor 143 used as a detector. Light 153 from the sources 151 strikes luminescent tags, and light 152 from the tags strikes the phototransistor 143, activating electronics 148.

Example 5

Integrated LED Light Source and Phototransistor Detection Device

An LED 161 is driven by an LED driver 160 as shown in FIG. 5. The light is collected by the base 173 of phototransistor 162. In one embodiment, the emitter 163 of phototransistor 162 is connected to a 5 V source. The current from collector 164 is converted to a voltage by transimpedence amplifier 167 (consisting of operational amplifier 165 with non-inverting input 175 tied to a 2.5 V source and feedback resistor 166) and then amplified by a gain stage 169 and a power amplifier 172. AC coupling with capacitor 170 and resistor 171 tied to ground is used to block the dc component of the signal. This circuit includes an LED for excitation. The circuit also can operate to detect pulsed or modulated light signals due to its AC coupling scheme.

Example 6

Layout of an Integrated Circuit for Implementing Light Source and Detection Device FIG. 6 illustrates an integrated circuit that may be used for implementing the light source and detection device of FIG. 1 or FIG. 5. Silicon die 183 with bonding pads 182 contains a GaAs infrared LED 161 that is driven by LED driver circuit 160. LED array 180 is multiplexed by multiplexer 181 to amplifiers 167 and 168. Detector 162 signal is amplified and compared to a reference level by comparator 184. This may be used to give a simple indication of the total level of fluorescence present.

A second embodiment of the present invention includes a large-area, 4×4 n-well integrated amplifier-photodiode array that is designed as a single, custom integrated circuit. This integrated circuit is coupled to a biosensor and is designed for monitoring very low light levels. FIG. 7 shows the physical layout of such an array. The sixteen individual photodiodes are 0.9 mm by 0.9 mm in size and are arranged on a 4 mm by 4 mm grid. FIG. 7 is an example of a 4×4 array of detectors which can be used in systems shown in FIGS. 21, 23, 25 and 29. The light sources are not shown in FIG. 7. The photodiodes and the accompanying electronic circuitry may be fabricated using a standard 1.2 micron n-well CMOS process such as that available from Orbit Semiconductor. The use of this type of standard process allows the production of photodiodes and phototransistors, as well as many other types of analog and digital circuitry, in a single integrated circuit. The photodiodes are produced using the n-well structure generally used to make resistors or the body material for a PMOS transistor. Details are shown in FIG. 8.

Example 7

Schematic Cross-Section of a N-Well Photodiode

FIG. 8 illustrates a schematic cross-section of an n-well photodiode that may be used in the photodiode array of FIG. 7. The light 203 travels through oxide layer 200. Since the anode 202 of the photodiode 190 is the p-type substrate material that is common to each circuit on the chip, only the cathode 201 is available for monitoring the photocurrent, and the photodiode is constrained to operate with a reverse bias.

Example 8

Detection Circuit

FIG. 9 shows a photodiode instead of phototransistor circuit that establishes reverse bias of photodiode includes adjustable gain 222. (Note that FIGS. 2 and 5 show phototransistors instead of photodiodes.) The operational amplifier 225 and the feedback resistor 227 form a transimpedence amplifier 221 that converts the current from the photodiode 220 (with anode 230 tied to ground and cathode 229 tied to the inverting input of operational amplifier 225) into a voltage. The conversion gain (in volts per amp) is determined by the value of the feedback resistor 227. The feedback capacitor 226 prevents the amplifier 221 from oscillating and limits the bandwidth of the circuit, which should generally be no greater than required to obtain the desired measurement. Reduction of the bandwidth decreases the noise that is present at the amplifier's output and thus, if the signal is not attenuated by the decreased bandwidth, results in a net gain of signal to noise ratio. The signal bandwidth for the circuit in FIG. 9 is $1/(2\pi R_1 C_1)$.

In one embodiment, feedback resistor 227 has a value of 1 MΩ and feedback capacitor 226 has a value of 100 pF. A bias voltage may be applied to the non-inverting input 228 of operational amplifier 225 to decrease the response time of photodiode 220. A low pass filter 224 and an adjustable gain 222 precede the analog to digital converter 223 and are included to improve the signal to noise ratio for very low frequency or dc signals. The voltage applied to the non-inverting input of the operational amplifier determines the reverse bias applied to the photodiode. The integrated circuit may be operated with a single 5 V supply. If 2 V are applied to the non-inverting input, then the DC level of the other input and the output will also be 2 V, so the reverse bias on the photodiode will be 2 V. Current flowing into the photodiode will also flow through the feedback resistor, causing the amplifier output to become more positive. Since the output of the operational amplifier cannot exceed the value of the positive voltage supply, the maximum output will be approximately 5 V. Thus, the maximum signal excursion will be 3 V, which corresponds to a maximum current of $3/R_1$.

Although this embodiment has illustrated one method for measuring low current levels, many other methods are possible and could be used without departing from the spirit and scope of the present invention. For example, one method of determining the current would be to integrate the current using an integrating amplifier for a fixed time and then measure the voltage or to integrate the current until a fixed voltage is reached and then measure the time. A second method to determine the current would be to use an oscillator. In particular, an integrator could continually integrate the unknown current until a preset a voltage was reached and then reset itself. The resulting frequency of oscillation would be proportional to the current. In addition to using standard CMOS capacitors, one could implement this second method using the capacitance of the photodiode itself. Initially, the switch is closed and the capacitance of the photodiode is discharged and there is zero voltage across the photodiode. When the switch is opened, light impinging on the photodiode creates charge which produces a voltage on the photodiode capacitance. More light increases the voltage which is amplified by the amplifier. When the output of the amplifier exceeds the reference voltage, the output of the comparator changes state, firing the one shot which in turn closes the switch and discharges the photodiode capacitance. This resets the amplifier input to the initial state and the comparator also returns to its initial state. When the one-shot times out, the switch opens and the process of charging can start again. A greater light level results in faster charging and therefore a higher frequency output of the oscillator. This results in an array of integrators that could be multiplexed to a single fast amplifier without the loss of significant measurement time.

Example 9

Alternative Detection Circuit

FIG. 10 shows an alternative detection circuit that may be used in conjunction with the photodiode array of FIG. 7. The circuit in FIG. 10 uses an integrating amplifier 240 in place of the transimpedence amplifier 221 in FIG. 9. The low pass filter 224 in FIG. 9 is not required since the integrator 240 in FIG. 10 is an automatically tracking low pass filter during each sample period. In FIG. 10, the integrator 240 integrates the current from the photodiode 220 until the signal is sampled, at which point the integrator 240 is cleared by closing reset switch 242. An advantage of this approach is that the integration time may be adapted to various light (and therefore current) levels. This approach requires coordination between the analog to digital conversion process and the integrator. The analog-to-digital converter must sample the output of the programmable gain amplifier when the integration time is completed and before the integrator is reset.

Example 10

Analog Multiplex

FIG. 11 shows an analog multiplexer 265 that may be used to allow any single element 266 in the photodiode array of FIG. 7 to be connected through output 267 to an amplifier 260. One possible implementation of this multiplexer for use with 16 elements is shown in FIG. 12. Each element 266 has a unique four bit address and two CMOS switches 286 and 287 that are controlled by the output of the cell's address decoder 280. Switch 286 is closed only when that particular cell is being addressed, and switch 287 is closed except when that particular cell is being addressed. In this way, the addressed photodiode is connected to one amplifier 260 through output 267 and the non-addressed photodiodes are connected in parallel to another amplifier 261 through output 268. Switch 286 is composed of parallel CMOS switches 282 and 283, and switch 287 is composed of parallel CMOS switches 284 and 285. One gate in each pair is controlled by the output of the address decoder and the other gate is controlled by the inverse 281 of the output of the address decoder. This configuration allows the switching of signals that range from the ground potential to the supply voltage. (The individual CMOS gates are not forward biased at the peak of the signal swing.)

Example 11

Light Source Array

Using the multiplexer in FIG. 11, FIG. 12 shows use of a 4×4 array of light sources (such as luminescent probes, for example) to be connected to a photodiode array from which signal levels are read sequentially. Using a single photodiode detector instead would require mechanical motion to scan the source array. The amplifier for the non-addressed photodiodes allows the charges from these photodiodes to be correctly biased and captured. Failure to use this amplifier may result in an erroneous measurement from the addressed photodiode due to its collection of currents from non-addressed photodiodes. Further, this multiplexed, dual amplifier approach allows the chip to function as a single, large area (nearly 4 mm square) photodetector.

For many applications, the low pass filter time constant is large in order to improve the signal to noise ratio. If the data are read sequentially, a large time constant can greatly increase the time needed to read the entire array. For example, if the time constant is set to 1 second and the array is 4×4, then the minimum time to acquire data would be 80 seconds, where a factor of 5 has been included to allow the amplifier and low pass filter to settle after their input is switched to another photodiode.

Example 12

Partial Parallel Method

As an alternative to the multiplexed method shown in FIG. 11 and FIG. 12, a partially parallel method may be used to obtain data from the photodiode array shown in FIG. 7. Such a partially parallel method is illustrated by FIG. 13. In this case, a row 310 of photodiodes 300 is multiplexed by multiplexer 301 into an amplifier 302 and a low pass filter 303. Columns or other sub-units of the array may be used in place of rows. The output of each low pass filter is input into a multi-channel analog to digital converter 304, which may be implemented on the same integrated circuit as the photodiode array, amplifier, and low pass filter. The A/D converter 304 produces output 305. For an n×n array, such a partially parallel method reduces the time required for a sequential method by a factor of n.

Example 13

Fully Parallel Readout

Yet another method that may be used to obtain data from the photodiode array shown in FIG. 7 is the fully parallel readout scheme shown in FIG. 14. In this case, each photodiode 320 is provided with its own amplifier 321, low pass filter 322, and analog to digital converter input 328. For an n×n array, such a fully parallel method reduces the time required for a sequential method by a factor of $n^2$.

One advantage of a custom biosensor integrated circuit is that the photodiodes may be made to physically match the probe. The embodiment of FIG. 7 uses 0.9 mm square photodiodes on a 1 mm by 1 mm square grid, but arrays with a larger number of smaller photodiodes are also possible. Using the readily available 1.2 micron technology, a 10 by 10 array may be made using photodiodes on a 20 micron grid, thereby providing 100 photodiodes in an area of only 0.04 $mm^2$, which is a density of 2500 photodiodes per $mm^2$. An even greater density is possible using 0.5 micron processes or 0.25-micron (or less) processes, which are also commercially available. These processes use lithographic methods to fabricate these submicron structures to allow greater density of photodetector and light source arrays.

Example 14

NIR Dye-Labeled Nucleic Acids

FIG. 15 shows a calibration curve for an NIR dye-labeled, single-stranded DNA (sequence: 5'-CCTCCTCCTTCCCAGCAGGG-3'; SEQ ID NO:3) over a concentration range from 1 pmol/$\mu$L to 3 fmol/$\mu$L. Excitation light was provided by a pen-size 9.5 mW laser diode (780 nm), and measurement times ranged from 1 to 3 minutes. Data were collected using a waveguide multiprobe system with a charge-coupled device (CCD) detector. This calibration curve was linear over the full range of the dye concentration investigated. The limit of optical detection, based on a signal equal to three times the standard deviation of the noise, was estimated to be in the range of 100 attomole/$\mu$L.

Example 15

Fluorescence Measurements on Tagged Gene Probes

FIG. 16 shows the results of measurements of gene probes tagged with fluorescein, a dye label emitting in the visible range. Measurement times ranged from 0.05 to 2 s. The results show that the calibration curve is linear down to a concentration of approximately 2 nmol/$\mu$L. The higher detection limit is attributable to an increase in background fluorescence of the waveguide in the visible region. The measurements were performed using the CCD detection system. The results demonstrate the possibility for quantitative analysis of fluorescein-labeled DNA probes.

Example 16

Signal Output Response for Fluorescent Dye

The present invention has been evaluated by measuring the fluorescence signal of a fluorescent dye spotted into the detector. FIG. 17 shows the performance of an ICM phototransistor and amplifier circuit consisting of a 2 $\mu$m, p-well CMOS process occupying an area of 160,000 square microns and 220 phototransistor cells connected in parallel. Shown in FIG. 17 is the signal output response for various concentrations of the dye label Rhodamine-6G excited with a small helium-cadmium laser (8 mW, 325 nm) illustrating the linearity of the microchip detector with respect to label concentration.

Example 17

Evaluation of 4×4 Array Integrated Chip

Figure 18:
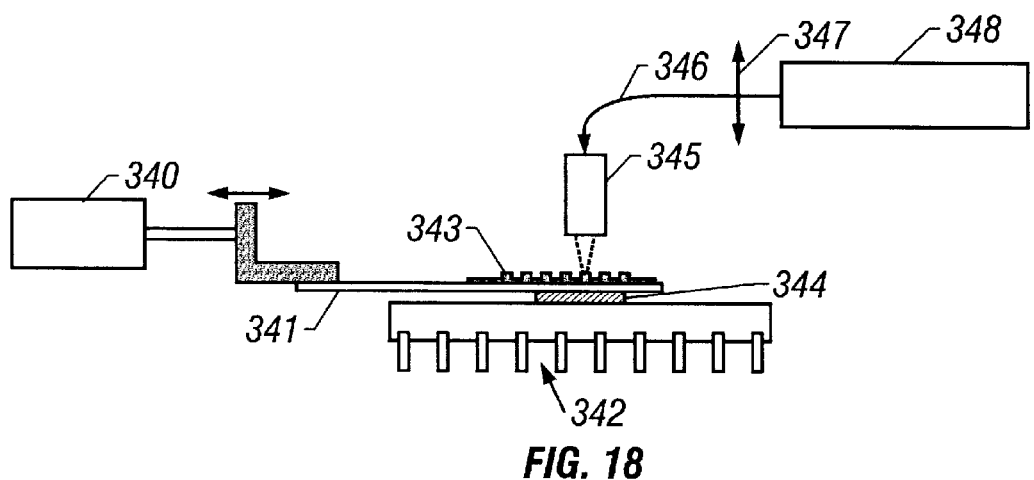
FIG. 18 illustrates schematically an experimental setup that may be used to evaluate a 4×4 array amplifier/phototransistor integrated circuit microchip device.

FIG. 18 illustrates a setup for the evaluation of a 4×4 array amplifier/phototransistor integrated circuit microchip (AP-ICM) device. The current in each channel was recorded using a digital photometer. The data from the photometer was transferred to a personal computer via a serial RS-232 line. The samples consisted of an array of microspots 343 of fluorescein-labeled DNA on a membrane. The membrane was placed on a glass slide 341 connected to a linear translation stage 340. The measurements were made while the translation stage moved the sample arrays over the stationary phototransistor device 342. Light from an argon ion laser 348 at 488 nm was transmitted via an optical fiber 346 through focusing optics 345 and 347 and was focused onto a sample spot. An appropriate optical filter 344 was placed between the sample substrate 343 and the detector array 342 in order to reject the laser radiation. The set-up described here was designed to evaluate the response of each individual photodetector on the chip. Application or systems are contemplated where multiple samples are scanned over individual detectors.

Example 18

Detection of DNAS Using the AP-ICM

FIG. 19 shows the results when four sample spots of 1 $\mu$L of fluorescein labeled DNA were placed on a nitrocellulose membrane that was translated over a detection channel of the AP-ICM device shown in FIG. 18. As the DNA spot passed over the photodetector, a fluorescence signal was detected. The four peaks in FIG. 19 illustrate the detection of the four DNA spots on the substrate by the AP-ICM device.

FIG. 20 shows the calibration curve of fluorescein-labeled DNA using the AP-ICM device shown in FIG. 18. The results demonstrate the capability of the AP-ICM chips to produce quantitative measurements of fluorescein-labeled DNA.

Example 19

Absorption and Reflection Measurements

Figure 21:
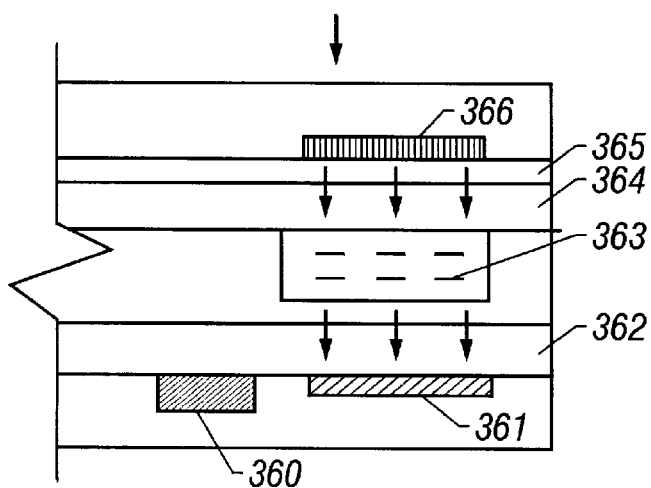
FIG. 21 illustrates an embodiment of the present invention that is used for absorption and reflection measurements.

FIG. 21 shows an embodiment of the present invention that is used for absorption and reflection measurements. Light from LED or diode laser 366 passes through an optional optical filter or lens stage 365 and the sample 363, which can be accessed through an optional sample inlet 364. Light from the sample 363 passes through an optical filter or lens stage 362 and impinges upon photodetector 361. Signal processor 360 receives the output from photodetector 361.

Example 20

Simultaneous Detection of Fluorescence and Raman

Figure 22:
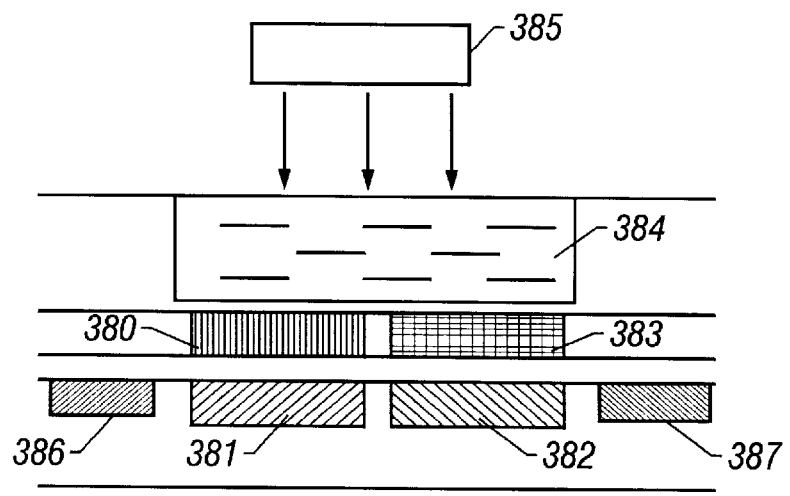
FIG. 22 is a schematic vertical section of a portion of a biochip of the invention that may operate with either luminescent or Raman radiation.

FIG. 22 shows an embodiment of the present invention that uses two photodetectors for simultaneous fluorescence and Raman measurements. Light from an excitation source 385 impinges upon sample 384. Light from sample 384 passes through the lens stage and optical filter 380 for fluorescence measurement and through the lens stage and optical filter 383 for Raman measurement. Light passing through lens stage and optical filter 380 is measured by photodetector 381 and processed by signal processor 386. Light passing through lens stage and optical filter 383 is measure by photodetector 382 and processed by signal processor 387.

Example 21

Multi-Detection Apparatus

Figure 23:
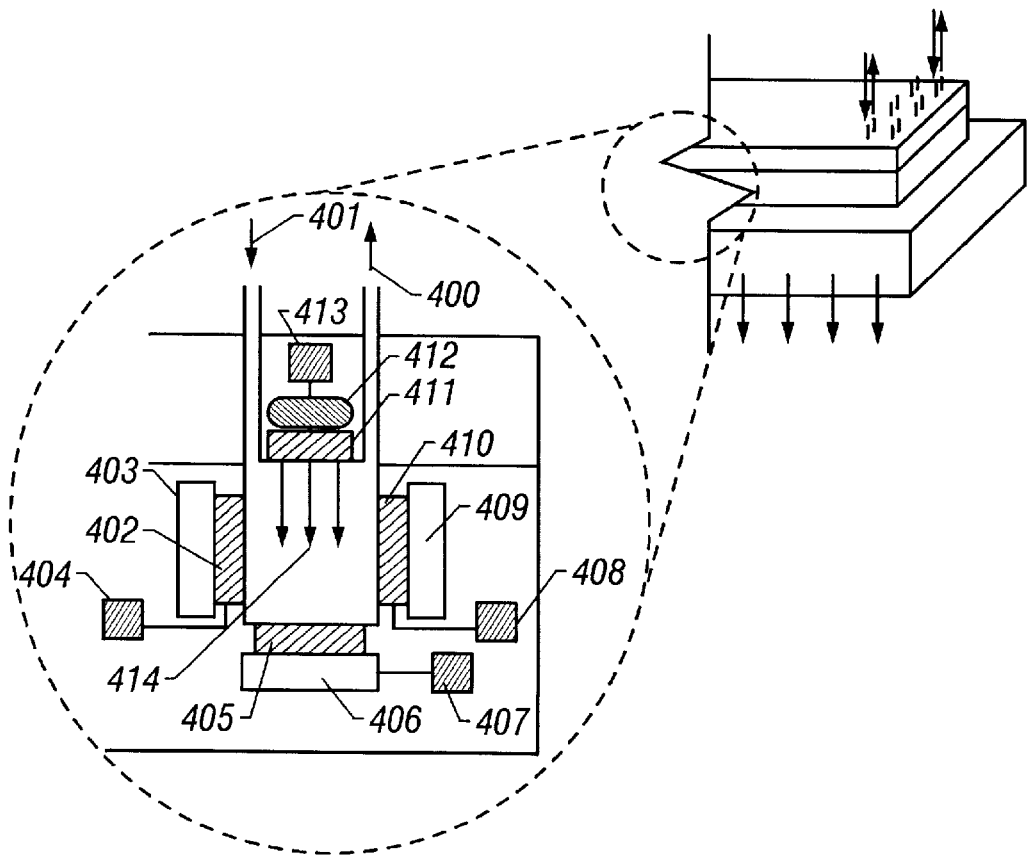
FIG. 23 is a schematic vertical section of a portion of a biochip that may employ luminescent or Raman energy for detection, or may operate by detecting the degree of absorption of a light beam.

FIG. 23 shows an embodiment of the present invention that uses three photodetectors for simultaneous absorption, fluorescence, and Raman measurements. A sample enters the sample chamber 414 through sample inlet 401 and exits through sample outlet 400. An LED or diode laser 412 receives power from a power supply 413 and directs light through an excitation filter 411 into sample chamber 414. Fluorescence measurements are made by optical filter and lens 402, photodetector 403, and signal processor 404. Absorption measurements are made by optical filter and lens 405, photodetector 406, and signal processor 407. Raman measurements are made by optical filter and lens 410, photodetector 409, and signal processor 408.

Example 22

Apparatus for Microfluidic Devices

Figure 24:
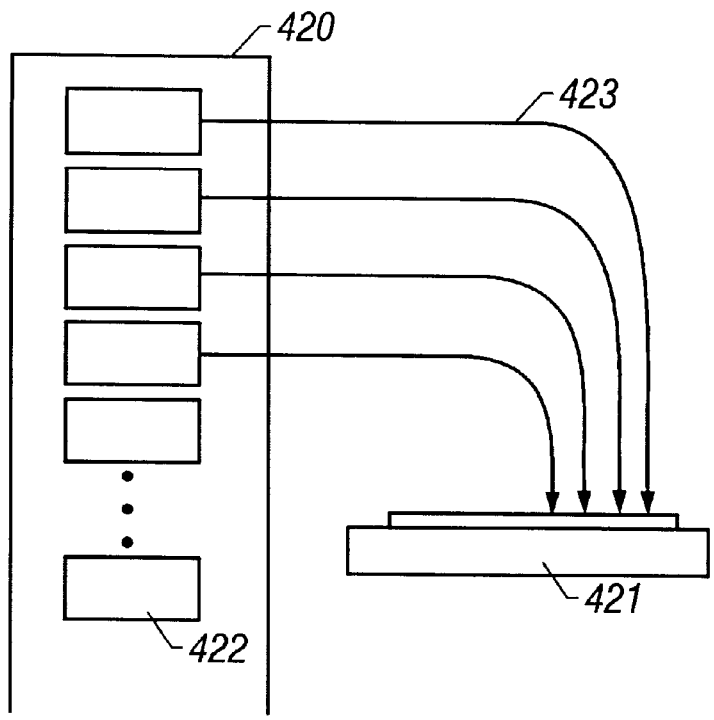
FIG. 24 illustrates a plan view of one embodiment of the present invention that is used to detect samples from a microfluidic device via a plurality of cells.

FIG. 24 shows an embodiment of the present invention that is used to detect samples from a microfluidic device such as a capillary electrophoresis array, a liquid chromatography array, a gas chromatography array, or a Lab-on-chip system. A microfluidic array 420 of microfluidic devices 422 direct samples through microfluidic channels 423 to the ICM chip 421.

Figure 25:
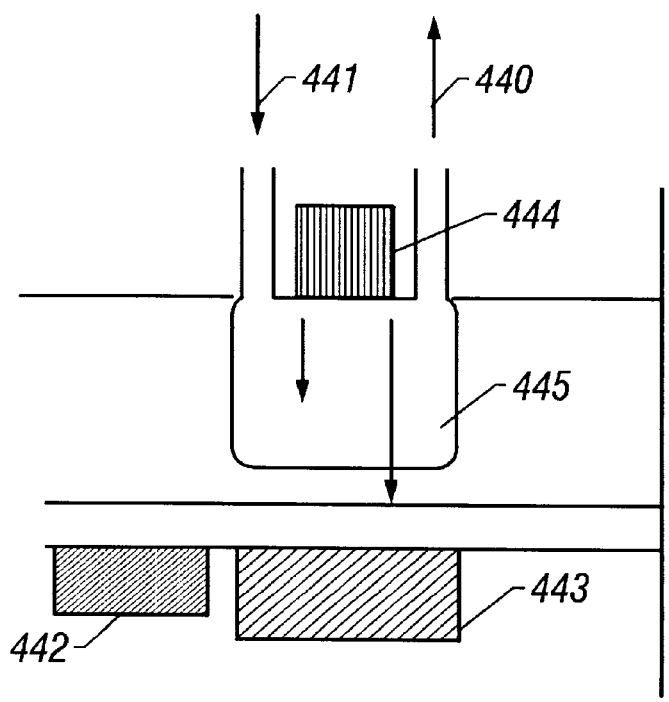
FIG. 25 illustrates a schematic vertical section of a microfluidic injection system for liquid and gas sample in and out of the ICM chip used in the embodiment illustrated by FIG. 24.

FIG. 25 Shows a detailed drawing of the ICM chip 421 used in the embodiment depicted by FIG. 24. The sample from the microfluidic device 422 enters sample chamber 445 through inlet 441 and exits through outlet 440. Light from LED 444 enters sample chamber 445, and the results are detected by photodetector 443 and signal processor 442.

Figure 26:
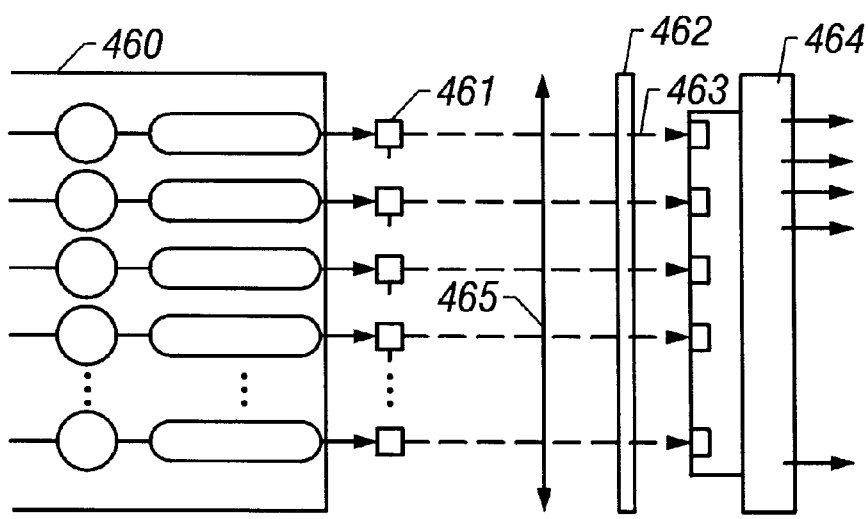
FIG. 26 illustrates an embodiment of the present invention that is used to detect samples from a microfluidic device using an imaging lens, binary optics, or a lens array to image each microfluidic channel onto a detector element of the ICM.

FIG. 26 shows an embodiment of the present invention that is used to detect samples from a microfluidic device using an imaging lens, binary optics, or a lens array to image each microfluidic channel onto a detector element of the ICM. Samples are directed from the microfluidics system 460 into sample chambers 461. Light from the sample chambers 461 is directed through imaging lens, binary optics, or lens array 465 and through an optical filter 462 onto photodetectors 463 on an ICM chip 464.

Example 23

Micro-Electromechanical Systems

Figure 27:
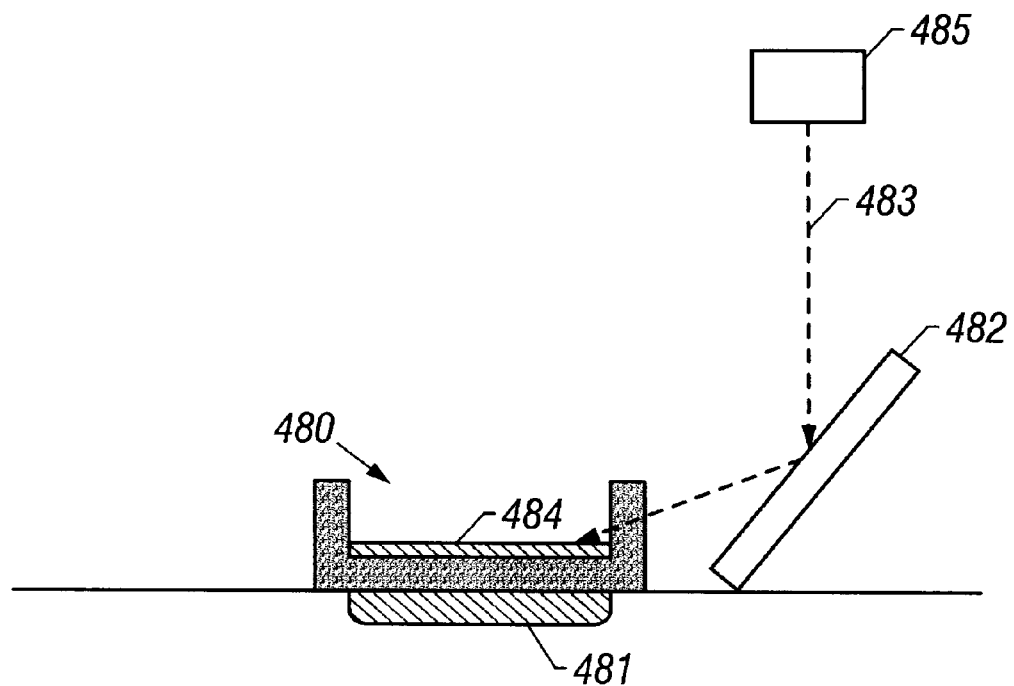
FIG. 27 illustrates a micro-electromechanical system (MEMS) that is used to construct an ICM with Random Access Microsensing.

FIG. 27 shows a micro-electromechanical system (MEMS) that is used to construct an ICM with Random Access Microsensing. Light 483 from laser 485 is directed toward an electrically positionable MEMs mirror 482, which then selectively directs the light onto DNA coated substrate 484 in a sample microchamber 480. The results are detected by a photodiode 481.

Figure 28:
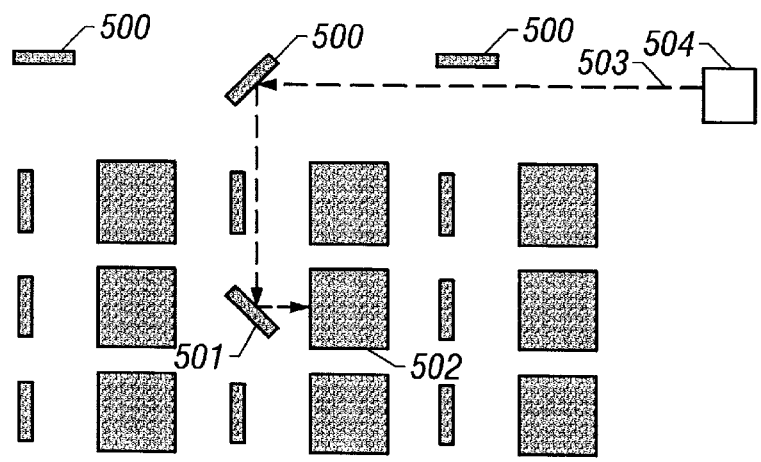
FIG. 28 illustrates an overview of an ICM system that uses the MEMS depicted in FIG. 27.

FIG. 28 shows an overview of an ICM system that uses the MEMS depicted in FIG. 27. Light 503 from laser 504 is selectively redirected by column select mirrors 500 onto a particular cell select mirror 501, which then directs the light into the corresponding biosensor cell 502. The mirrors as well as the diodes are etched and formed from silicon. The general fabrication steps for MEMs are similar to IC fabrication procedures using lithographic techniques. For MEMs, additional etching steps are performed to free to movage devices (e.g. mirrors) from the substrate. The mirrors allow the light from the laser 504 to be directed toward any individual biosensor cell.

Example 24

Vertical-Cavity Surface-Emitting Laser Apparatus

FIG. 29 shows an embodiment of the present invention that uses individually addressable, integrated vertical-cavity surface-emitting lasers (VCSEL) and on-axis and/or off-axis diffractive lenses. The linearity of VCSEL arrays make them ideal for compact two-dimensional and three-dimensional configuration in ICM systems. The ability to shape a diverging beam from a surface-emitting laser or an LED is important for micro-optic illumination in ICM systems. The diffractive optical element (DOE) system shown in FIG. 29 allows for this ability and, as shown, may be integrated and fabricated with a VCSEL onto a single transparent substrate. Such a compact source-diffractive lens is ideal for a miniature optical ICM array. Note, as shown in FIG. 29, that a DOE system can be constructed to produce either on-axis or off-axis beams. An on-axis configuration is suitable for absorption measurements, whereas an off-axis configuration is suitable for emission measurements. The off-axis beam can be constructed so that it does not impinge the detector, thus minimizing scattered light.

Light from the VCSEL array 520 is directed through beam waists 522 constructed on the GaAs substrate 523 and then through either an on-axis diffractive lens 521 or an off-axis diffractive lens 524. The results from sample chamber 525 are detected by photodetector 526.

REFERENCES

The following references, to the extent that they provide exemplary procedural or other details supplementary to those set forth herein, are specifically incorporated herein by reference.

Affymetrix http://www.affymetrix.com; Jul. 23, 1997.

J. P. Alarie, D. L. Stokes, W. S. Sutherland, A. C. Edwards, and T. Vo-Dinh, "Intensified charge coupled device-based fiber-optic monitor for rapid remote surface-enhanced Raman scattering sensing," *Appl. Spectrosc.,* 46, 1608–1612, 1992.

P. Aubert, H. Oguey and R. Vuillcumier, "Monolithic Optical Position Encoder with On-Chip Photodiodes," *IEEE Journal of Solid State Circuits*, Vo. 23, No.2, pp. 465–73, 1988.

M. Eggars, M. Hogan, R. K. Reich, J. Lamture, D. Ehrlich, M. Hollis, B. Kosicki, T. Powdrill, K. Beattie, S. Smith, R. Varma, R. Gangadharam, A. Mallik, R. Burke, and D. Wallace, "A microchip for quantitative detection of molecules utilizing luminescent and radioisotope reporter groups," *Biotechniques,* 17, 516–523, 1994.

R. L. Geiger, P. E. Allen and N. R. Strader, "VLSI Design Techniques for Analog and Digital Circuits", McGraw-Hill Publishing Co., New York, 1990.

C. R. Graham, D. Leslie, and D. J. Squirrell, "Gene probe assay on a fibre-optic evanescent wave biosensor," *Biosensors and Bioelectronics* 7, 487–493, 1992.

N. R. Isola, J. P. Alerie, G. D. Griffin and T. Vo-Dinh, "Development of a Ganasensor for Mycobacterium Tuberculosis" in *Biomedical Sensing Imaging and Tracking Technologies I, Eds*. Lieberman, R. A.., Vo-Dinh, T., Poblbieska H., SPIE, Vol. 2676, pp 228–239, (1996).

P. Kumar, R. C. Wilson, J. J. Valdes, and J. P. Chambers, "Monitoring oligonucleotide hybridization using light-addressable potentiometric and evanescent wave fluorescence sensing," *Materials Science and Engineering*, C1, 187–192, 1994.

P. A. E. Piunno, U. J. Krull, R. H. E. Hudson, M. J. Damha, and H. Cohen, "Fiber optic biosensor for fluorimetric detection of DNA hybridization," *Anal. Chim. Acta,* 228, 205–214, 1995.

R. K. Saiki, D. H. Gelfand, S. Stoffel, S. J. Scharf, R. Higuchi, G. T. Horn, K. B. Mullis, and H. A. Erlich, "Prime-directed enzymatic amplification of DNA with a thermostable DNA polymerase," *Science,* 239, 487–491, 1988.

M. Schena, D. Shalon, R. W. Davis, and P. O. Brown, "Quantitative monitoring of gene expression patterns with a complementary DNA microarray," *Science* 270, 467–470, 1995.

H. Sigust, et al., "Surface Immobilization of Biomolecules by Light", *Optical Engineering*, 34, 2338, 1995.

C. L. Stevenson, R. W. Johnson, and T. Vo-Dinh, "Synchronous luminescence: A New Detection Technique for Multiple Probes used for DNA Sequencing," *Biotechniques* 16, 1104–1110, 1994.

T. Vo-Dinh, B. J. Tromberg, G. D. Griffin, K. R. Ambrose, M. J. Sepaniak, and E. M. Gardenhire, "Antibody-based Fiberoptics Biosensor for the Carcinogen Benzo(a)pyrene", *Appl. Spectrosc.,* 5, 735–738, 1987.

T. Vo-Dinh, G. D. Griffin, and M. J. Sepaniak, "Fiber optic fluoroimmunosensors," in *Fiber Optic Chemical Sensors and Biosensors*, O. S. Wolfbeis, ed., CRC Press, Boca Raton, Fla., 1991.

T. Vo-Dinh, K. Houck, and D. L. Stokes, "Surface-enhanced Raman gene probes," *Anal. Chem.,* 66, 3379–3383, 1994.

T. Vo-Dinh, *Room Temperature Phosphorimetry for Chemical Analysis*, John Wiley, New York, 1989.

Although the present invention has been described in detail, it should be understood that various changes, substitutions, and alterations can be made hereto by one skilled in the art without departing from the spirit and scope of the invention as defined by the appended claims.

What is claimed is:

1. An integrated circuit microchip sensor that detects a target biomolecule, the integrated circuit microchip sensor comprising:
   a probe that specifically binds to the target biomolecule;
   a solid support to which the probe is secured;
   at least one sensor connected to the probe, wherein the probe generates a detection signal, existing at a signal level related to a level of electromagnetic radiation detected by the sensor;
   a membrane positioned between the probe and the sensor, the membrane being capable of filtering the electromagnetic radiation;
   a lens secured to the solid support and positioned between the probe and the sensor; and
   detection circuitry connected to at least one sensor for processing the detection signal, and for generating an output signal proportional to the detection signal, wherein the signal indicates the presence of the biomolecule in the sample.

2. The integrated circuit microchip sensor of claim 1, wherein the membrane is positioned between the lens and the probe.

3. The integrated circuit microchip sensor of claim 1, wherein the probe binds to a nucleic acid, an antibody, an enzyme, a polypeptide, or a peptide.

4. The integrated circuit microchip sensor of claim 1, wherein the probe includes a source of electromagnetic radiation.

5. The integrated circuit microchip sensor of claim 4, wherein the source of electromagnetic radiation includes a light emitting diode or a semiconductor laser.

6. The integrated circuit microchip sensor of claim 1, wherein the target molecule comprises a source of electromagnetic radiation.

7. The integrated circuit microchip sensor of claim 1, wherein the electromagnetic radiation detected by the sensor is radiated in the visible, ultraviolet, infrared, near-infrared, x-ray, or radio frequency spectrum.

8. The integrated circuit microchip sensor of claim 1, wherein the sensor includes a discrete detector.

9. The integrated circuit microchip sensor of claim 8, wherein the discrete detector comprises a phototransistor, an avalanche diode, or a photodiode.

10. The integrated circuit microchip sensor of claim 1, wherein the sensor includes a photodetector.

11. The integrated circuit microchip senior of claim 10, wherein the photodetector comprises a phototransistor, an avalanche diode, or a photodiode.

12. The integrated circuit microchip of claim 1, wherein the detection circuitry includes a transimpedance amplifier converting the generated signal from a current signal to a voltage signal.

13. The integrated circuit microchip of claim 12, wherein the detection circuitry further includes at least one of an amplifier amplifying the converted voltage signal, a low-pass filter and adjustable gain combination, and an adjustable gain.

14. The integrated circuit microchip sensor of claim 1, further comprising a two-dimensional array of probes including the probe.

15. The integrated circuit microchip sensor of claim 14, further comprising a two-dimensional array of sensors including the sensor, the two-dimensional array of sensors corresponding to the two-dimensional array of probes.

16. The integrated circuit microchip sensor of claim 14, wherein the two-dimensional array is one 4 probes×4 probes or 10 probes by 10 probes.

17. A method of detecting a biomolecule comprising:
    contacting a sample suspected of containing the biomolecule with the integrated circuit microchip sensor of claim 1; and
    detecting the presence of an output signal from the sensor, wherein the presence of the output signal is indicative of the presence of the biomolecule in the sample.

* * * * *